(12) United States Patent
Hibner

(10) Patent No.: US 7,753,857 B2
(45) Date of Patent: Jul. 13, 2010

(54) TISSUE SAMPLE SERIAL CAPTURING BIOPSY DEVICE

(75) Inventor: John A. Hibner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/753,665

(22) Filed: May 25, 2007

(65) Prior Publication Data

US 2007/0255174 A1    Nov. 1, 2007

Related U.S. Application Data

(63) Continuation-in-part of application No. 10/953,834, filed on Sep. 29, 2004, now abandoned.

(51) Int. Cl.
*A61B 10/00* (2006.01)

(52) U.S. Cl. .................................... 600/566

(58) Field of Classification Search ................ 600/562, 600/564, 565, 658, 571, 568
See application file for complete search history.

(56) References Cited

U.S. PATENT DOCUMENTS

| | | |
|---|---|---|
| 3,917,086 A | 11/1975 | Sexton |
| 3,994,297 A | 11/1976 | Kopf |
| 5,526,822 A | 6/1996 | Burbank et al. |
| 5,532,168 A | 7/1996 | Marantz |
| 5,649,547 A | 7/1997 | Ritchart et al. |
| 5,769,086 A | 6/1998 | Ritchart et al. |
| 5,775,333 A | 7/1998 | Burbank et al. |
| 5,873,967 A | 2/1999 | Clark et al. |
| 5,928,164 A | 7/1999 | Burbank et al. |
| 5,964,716 A | 10/1999 | Gregoire et al. |
| 5,980,469 A | 11/1999 | Burbank et al. |
| 6,007,497 A | 12/1999 | Huitema |
| 6,017,316 A | 1/2000 | Ritchart et al. |
| 6,042,593 A | 3/2000 | Storz et al. |
| 6,077,230 A | 6/2000 | Gregoire et al. |

(Continued)

FOREIGN PATENT DOCUMENTS

WO    WO 2004/075728    9/2004

OTHER PUBLICATIONS

EPO Search Report, Application No. 05256035.6, pp. 1-6.

(Continued)

*Primary Examiner*—Max Hindenburg
*Assistant Examiner*—Fangemonique Smith
(74) *Attorney, Agent, or Firm*—Frost Brown Todd LLC

(57) ABSTRACT

A biopsy device and method are provided for obtaining a tissue sample, such as a breast tissue biopsy sample. The biopsy device includes a disposable probe assembly with an outer cannula having a distal piercing tip, a cutter lumen, and a cutter tube that rotates and translates past a side aperture in the outer cannula to sever a tissue sample. The biopsy device also includes a reusable handpiece with an integral motor and power source to make a convenient, untethered control for use with ultrasonic imaging. The reusable handpiece incorporates a probe oscillation mode to assist when inserting the distal piercing tip into tissue. The motor also actuates an attached tape indexing mechanism in coordination with movement of the cutter tube to provide sequentially stored tissue samples in a replaceable serial stacking assembly.

9 Claims, 27 Drawing Sheets

U.S. PATENT DOCUMENTS

| | | | |
|---|---|---|---|
| 6,086,544 | A | 7/2000 | Hibner et al. |
| 6,120,462 | A | 9/2000 | Hibner et al. |
| 6,228,055 | B1 | 5/2001 | Foerster et al. |
| 6,231,522 | B1 | 5/2001 | Voegele et al. |
| 6,273,862 | B1 | 8/2001 | Privitera et al. |
| 6,428,486 | B2 | 8/2002 | Ritchart et al. |
| 6,436,054 | B1 * | 8/2002 | Viola et al. .................. 600/562 |
| 6,485,436 | B1 | 11/2002 | Truckai et al. |
| 6,638,235 | B2 | 10/2003 | Miller et al. |
| 7,025,732 | B2 | 4/2006 | Thompson et al. |
| 7,189,206 | B2 | 3/2007 | Quick et al. |
| 7,276,032 | B2 | 10/2007 | Hibner |
| 7,278,991 | B2 | 10/2007 | Morris et al. |
| 2002/0029007 | A1 * | 3/2002 | Bryan et al. ................ 600/565 |
| 2003/0125639 | A1 | 7/2003 | Fisher et al. |
| 2003/0199753 | A1 | 10/2003 | Hibner et al. |
| 2003/0199787 | A1 * | 10/2003 | Schwindt ................... 600/568 |
| 2004/0153003 | A1 | 8/2004 | Cicenas |
| 2004/0167428 | A1 | 8/2004 | Quick et al. |
| 2005/0065453 | A1 | 3/2005 | Shabaz et al. |
| 2005/0203439 | A1 | 9/2005 | Heske et al. |
| 2005/0215921 | A1 | 9/2005 | Hibner |
| 2006/0074342 | A1 | 4/2006 | Hibner |
| 2006/0074343 | A1 | 4/2006 | Hibner |
| 2006/0074344 | A1 | 4/2006 | Hibner |
| 2006/0074345 | A1 | 4/2006 | Hibner |
| 2006/0260994 | A1 | 11/2006 | Mark et al. |
| 2007/0032741 | A1 | 2/2007 | Hibner et al. |
| 2007/0032743 | A1 | 2/2007 | Hibner |
| 2007/0239067 | A1 | 10/2007 | Hibner et al. |

OTHER PUBLICATIONS

European Patent Office Communication dated Jun. 25, 2007 for Application No. 05256035.

* cited by examiner

TISSUE SAMPLE SERIAL CAPTURING BIOPSY DEVICE

CROSS REFERENCE TO RELATED APPLICATIONS

The present application is a continuation-in-part of the co-pending and commonly-owned U.S. patent application Ser. No. 10/953,834, "BIOPSY APPARATUS AND METHOD" to Hibner et al., filed 29 Sep. 2004 (U.S. Pat. Publ. No. 2006/0074345), the disclosure of which is hereby incorporated by reference in its entirety.

FIELD OF THE INVENTION

The present invention relates in general to biopsy devices, and more particularly to biopsy devices having a cutter for severing tissue, and even more particularly to biopsy devices for multiple sampling with a probe remaining inserted.

BACKGROUND OF THE INVENTION

When a suspicious tissue mass is discovered in a patient's breast through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

An open biopsy is performed by making a large incision in the breast and removing either the entire mass, called an excisional biopsy, or a substantial portion of it, known as an incisional biopsy. An open biopsy is a surgical procedure that is usually done as an outpatient procedure in a hospital or a surgical center, involving both high cost and a high level of trauma to the patient. Open biopsy carries a relatively higher risk of infection and bleeding than does percutaneous biopsy, and the disfigurement that sometimes results from an open biopsy may make it difficult to read future mammograms. Further, the aesthetic considerations of the patient make open biopsy even less appealing due to the risk of disfigurement. Given that a high percentage of biopsies show that the suspicious tissue mass is not cancerous, the downsides of the open biopsy procedure render this method inappropriate in many cases.

Percutaneous biopsy, to the contrary, is much less invasive than open biopsy. Percutaneous biopsy may be performed using fine needle aspiration (FNA) or core needle biopsy. In FNA, a very thin needle is used to withdraw fluid and cells from the suspicious tissue mass. This method has an advantage in that it is very low-pain, so low-pain that local anesthetic is not always used because the application of it may be more painful than the FNA itself. However, a shortcoming of FNA is that only a small number of cells are obtained through the procedure, rendering it relatively less useful in analyzing the suspicious tissue and making an assessment of the progression of the cancer less simple if the sample is found to be malignant.

During a core needle biopsy, a small tissue sample is removed allowing for a pathological assessment of the tissue, including an assessment of the progression of any cancerous cells that are found. The following patent documents disclose various core biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al.

At present, a biopsy instrument marketed under the trade name MAMMOTOME is commercially available from ETHICON ENDO-SURGERY, INC. for use in obtaining breast biopsy samples. This device generally retrieves multiple core biopsy samples from one insertion into breast tissue with vacuum assistance. In particular, a cutter tube is extended into a probe to cut tissue prolapsed into a side aperture under vacuum assistance and then the cutter tube is fully retracted between cuts to extract the sample.

With a long probe, the rate of sample taking is limited not only by the time required to rotate or reposition the probe but also by the time needed to translate the cutter. As an alternative to this "long stroke" biopsy device, a "short stroke" biopsy device is described in the following commonly assigned patent applications: U.S. patent application Ser. No. 10/676,944, "Biopsy Instrument with Internal Specimen Collection Mechanism" filed Sep. 30, 2003 in the name of Hibner et al.; and U.S. patent application Ser. No. 10/732,843, "Biopsy Device with Sample Tube" filed Dec. 10, 2003 in the name of Cicenas et al. The cutter is cycled across the side aperture, reducing the sample time. Several alternative specimen collection mechanisms are described that draw samples through the cutter tube, all of which allow for taking multiple samples without removing the probe from the breast.

In particular, the above cross referenced patent application and in U.S. patent application Ser. No. 10/953,834, "BIOPSY APPARATUS AND METHOD", the disclosure of which is hereby incorporated by reference in its entirety, these tissue samples are drawn by vacuum proximally through the cutter tube into a serial tissue stacking assembly that preserves the order of sample taking, can be visually observed through a transparent lumen, and serves as a transport container to take the samples for a pathology examination.

While these known tissue storage approaches have a number of advantages, it is believed that further improvements may be made to tissue storage and transport for core biopsy procedures.

SUMMARY OF THE INVENTION

The present invention addresses these and other problems of the prior art by providing a biopsy device that has a probe cannula that is inserted into tissue to obtain a core biopsy sample by translating a cutter with the probe cannula. A pneumatic pressure differential is used to draw a severed tissue sample proximally from the probe cannula into a proximal stacking tube that provides confirmation of successful sample collection, preserves the sequential order of the samples, allows multiple samples to be taken without reinserting the probe cannula, provides a convenient holder for on-site scans for calcifications, and avoids a biohazard as the samples are taken to a pathology assessment.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

Figure 1:
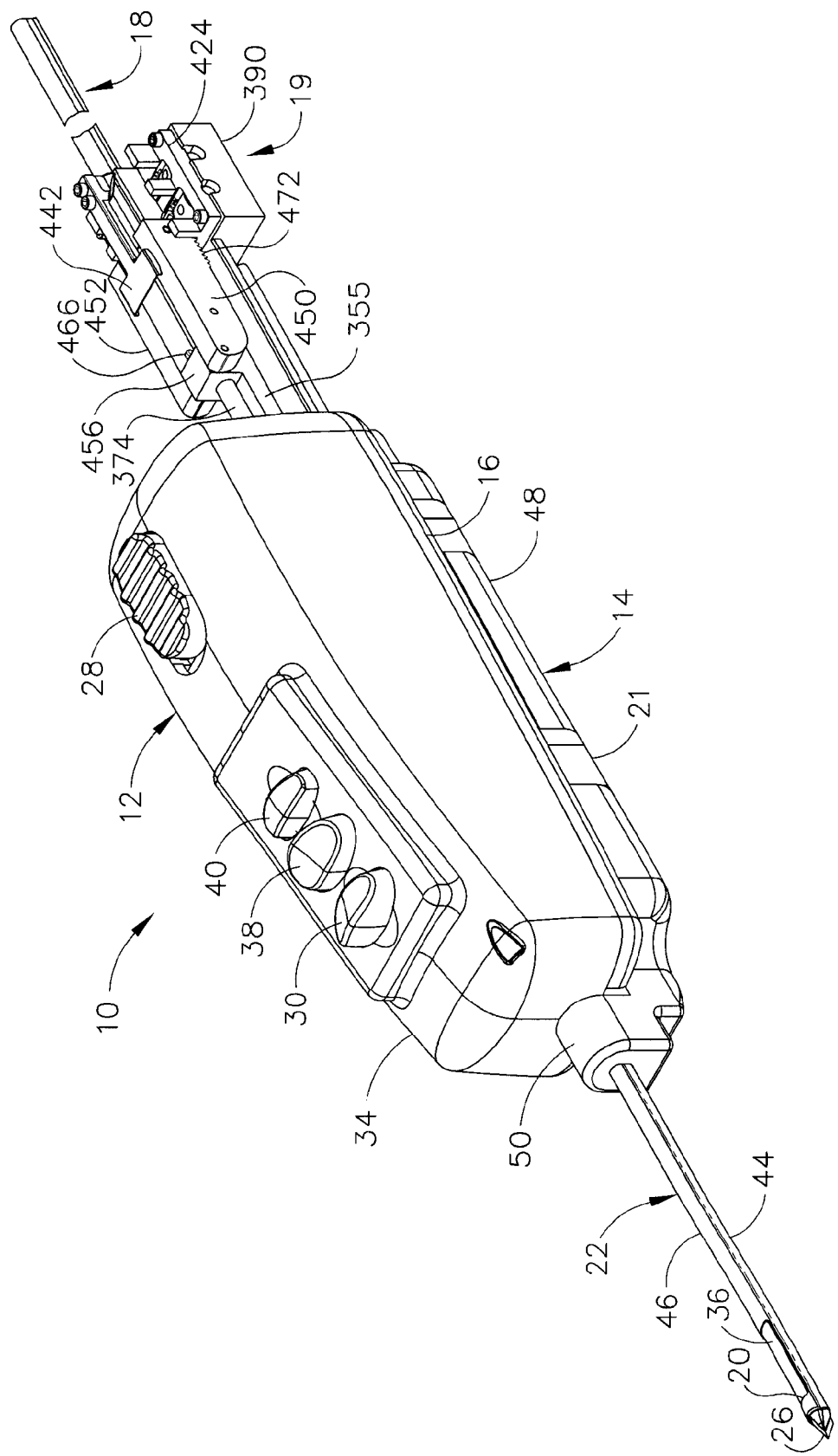
FIG. 1 is an isometric view of a biopsy device with an attached serial tissue stacking assembly.
Figure 2:
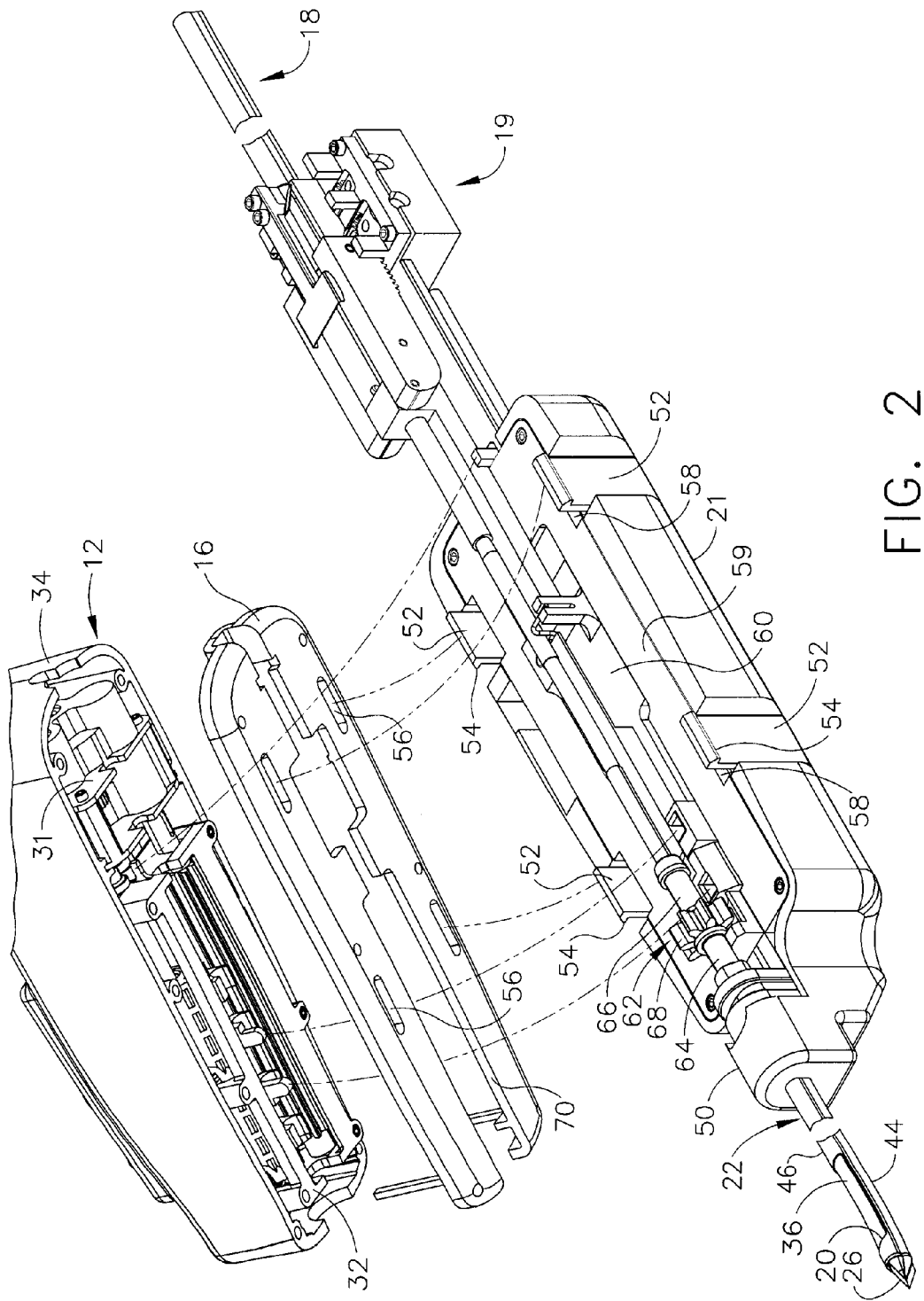
FIG. 2 is an isometric view of the biopsy device of FIG. 1 with a disposable probe assembly that includes the serial tissue stacking assembly disengaged from a reusable handpiece that has a lower tray removed to expose a carriage frame assembly and a motor drive assembly.

Turning to the Drawings, wherein like numerals denote like components throughout the several views, in FIGS. 1-2, a biopsy device 10 includes a reusable handpiece 12, and a disposable probe assembly 14. A lower handle tray 16 is disassembled from upper portions of the reusable handpiece 12 to expose portions that operably engage the disposable probe assembly 14. A replaceable serial tissue stacking assembly 18 is prepared to receive the next tissue sample by a tape indexing assembly 19 attached to a hand-held distal portion 21 of the disposable probe assembly 14 that mounts to and is actuated by the reusable handpiece 12. Tissue that is drawn by vacuum assistance into a side aperture 20 of a probe cannula 22 of the disposable probe assembly 14 is severed by a DC motor 24 (FIG. 3) in the reusable handpiece 12 that also powers rotation and staging of the serial tissue stacking assembly 18 to serially stack and store the tissue samples in the order received.

With particular reference to FIG. 1, insertion of the probe cannula 22 into tissue is integrally supported by a piercing tip 26 attached at a distal end as well as a longitudinal jack hammer motion to the probe cannula 22 selected by positioning a slide button 28 distally and depressing a forward motor button 30. In response, the DC motor 24 drives a transmission section 31 (FIG. 2) grounded to a top cover 34 of the reusable handpiece 12 to longitudinally reciprocate an internal carriage frame assembly 32 (FIG. 2) that is engaged for movement with the probe cannula 22. With the slide button 28 proximally positioned, depression of the forward motor button 30 causes the DC motor 24 to advance and rotate a cutter tube 36, depicted in FIG. 1 as having been fully distally translated, closing the side aperture 20. Depression of a reverse motor button 38 causes the cutter tube 36 to retract. Depression of a mode button 40 may cause other functions to be performed. Vacuum assistance passes through a lateral lumen 44 of the probe cannula 22 and distally communicates via internal vent holes 47 (FIG. 22) entering a cutter lumen 46 that encompasses the cutter tube 36 and includes the side aperture 20. An additional feature contemplated but not depicted includes using the mode button 40 to selectively communicate a saline supply to lateral lumen 44 to flush the probe cannula. It should be appreciated that the biopsy device 10 includes a minimum of "tethers" that would impede use, pose a tripping hazard, or extend set-up time.

Alternatively, instead of "hard-walled" lateral lumen 44 separated from the cutter lumen 46 along its length, applications consistent with the present invention may have a cylindrical probe cannula wherein the cutter tube 36 is positioned off-center to translate across a side aperture. A "soft-walled" lateral lumen may then be defined as a space between an outer diameter of the cutter tube and an inner diameter of the cylindrical probe cannula.

In FIG. 2, the disposable probe assembly 14 has a bottom cover 48 with a distal probe mount cover 50 that assists in supporting the probe cannula 22 while allowing the longitudinal jack hammer motion. A plurality of locking tabs 52 with locking edges 54 extend upwardly through pass through slots 56 formed in the periphery of the lower handle tray 16 to resiliently extend outwardly into engaging contact with the slots 56. Relieved areas 58 are formed behind each locking tab 52 in a top extension member 59 that surrounds a probe support body 60, the combination covering a cavity defined by the bottom cover 48, which allows depression of the locking tabs 52 to unlock the disposable probe assembly 14 to install another identical or similar assembly.

A proximal end of the cutter tube 36 receives a cutter gear 62 having distal and proximal reduced diameter bearing surfaces 64, 66 on each longitudinal side of a rotation spur gear section 68, which engage the reusable handpiece 12 for rotation and for longitudinal translation through a distally open longitudinal aperture 70 formed in the lower handle tray 16.

REUSABLE HANDPIECE. In FIGS. 3-12, the reusable handpiece 12 is depicted in various states of disassembly to illustrate its operation. The transmission section 31 is part of a rigidly mounted motor drive assembly 76 that includes the motor 24 in between a planetary gearbox 78 and an encoder 80. Battery or other power sources and control circuitry are omitted in the depictions. The motor drive assembly also includes a right guide pin 82 and a left guide pin 84. The motor drive assembly 76 is shown operably engaged to the longitudinally reciprocating carriage frame assembly 32 in FIG. 3 and disassembled from the longitudinally reciprocating carriage frame assembly in FIG. 4. In FIG. 4, the right guide pin 82 is inserted proximally through a right front pin guide 86 and then through a right rear pin guide 88 both part of an upper frame 90 of the carriage frame assembly 32. A proximal end of the right guide pin 82 resides within a distally projecting right pin receptacle 92 (FIG. 12) formed as part of a distal bulkhead 94 of the transmission section 31. A distal end of the right guide pin 82 is received by a right pin recess 96 (FIG. 5) formed in the top cover 34. Similarly, the left guide pin 84 is inserted proximally through a left front pin guide 98 and then through a left rear pin guide 100, both part of the upper frame 90 of the carriage frame assembly 32. A proximal end of the left guide pin 84 resides within a distally projecting left pin receptacle 102 respectively formed as part of the distal bulkhead 94 of the transmission section 31. A distal end of the left guide pin 84 is received by a left pin recess 104 (FIG. 5) formed in the top cover 34.

With particular reference to FIGS. 3, 4, 6, 7 and 12, a right front ring bearing 106 is inserted over a distal portion of the right guide pin 82 and is received within a cylindrical recess 108 formed on a distal side of the right front pin guide 86. A right aft ring bearing 109 is inserted over a proximal portion of the right guide pin 82 and is received within a cylindrical recess 111 (FIG. 6) formed on a proximal side of the right aft pin guide 88. A left front ring bearing 110 is inserted over a distal portion of the left guide pin 84 and is received within a cylindrical recess 112 formed on a distal side of the left front pin guide 98. A left aft ring bearing 113 (FIG. 9) is inserted over a proximal portion of the left guide pin 84 and is received within a cylindrical recess 115 (FIG. 6) formed on a proximal side of the left aft pin guide 100 A right compression spring 114 is proximally received over the right guide pin 82 between the right front and rear pin guides 86, 88. More particularly, the right compression spring 114 is distally positioned against the right front pin guide 86 and at its proximal end by a right downwardly projecting structure 116 (FIG. 5) formed on an interior of the top cover 34 that closely encompasses a top portion of the right guide pin 82 without contacting other portions of the carriage frame assembly 32. A left compression spring 118 is proximally received over the left guide pin 84 between the left front and rear pin guides 98, 100. More particularly, the left compression spring 118 is distally positioned against the left front pin guide 98 at its distal end by a left downwardly projecting structure 120 (FIG. 5) formed on the interior of the top cover 34 that closely encompasses a top portion of the left guide pin 84 without contacting other portions of the carriage frame assembly 32. Thereby, the carriage frame assembly 32 is biased to a distal position relative to the top cover 34 and lower handle tray 16.

Figure 3:
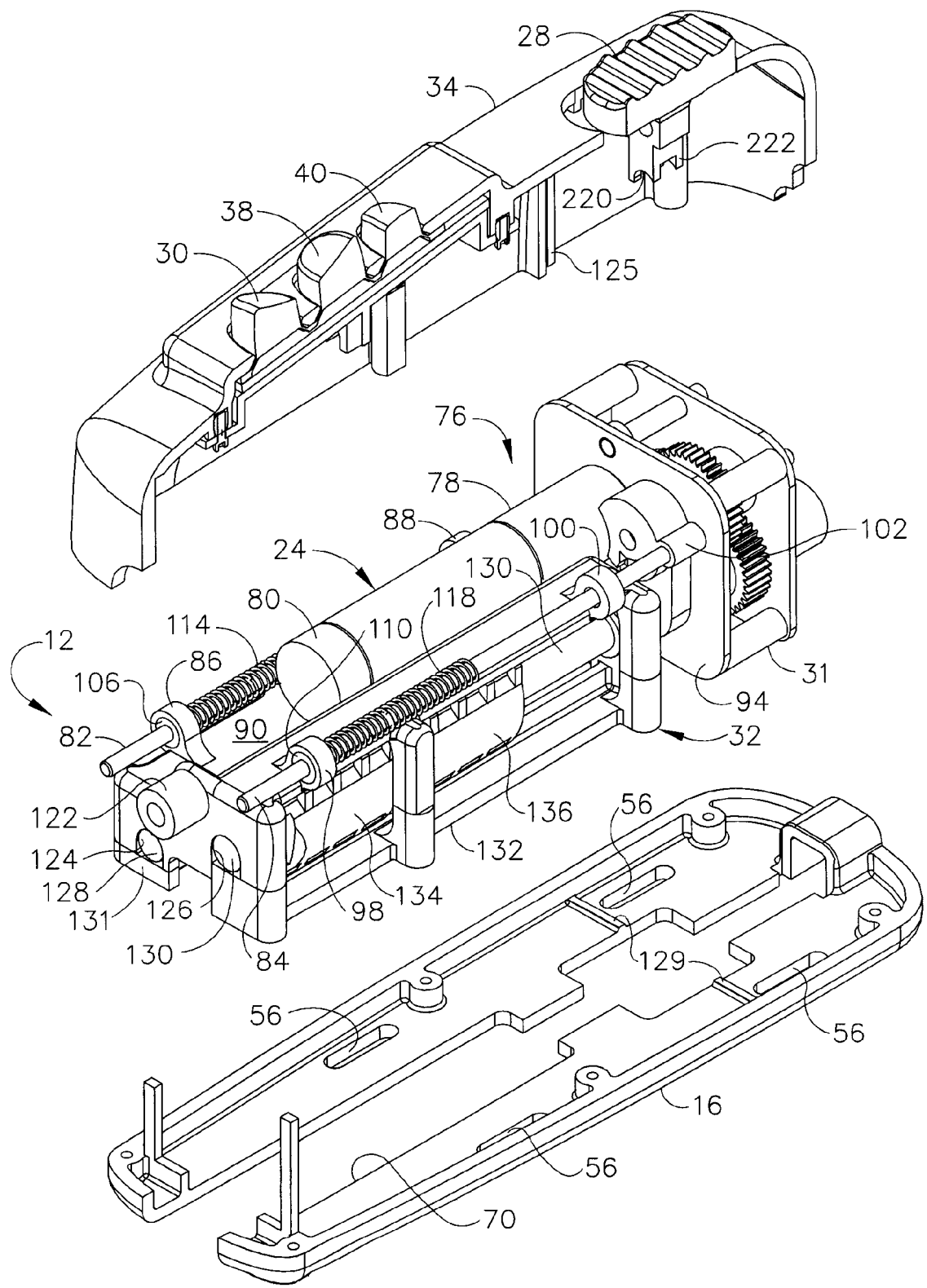
FIG. 3 is an isometric view of the reusable handpiece of FIG. 1 with a top cover detached with a left half cut away and with the lower handle tray detached to expose the motor drive assembly operatively engaged to the carriage frame assembly.
Figure 4:
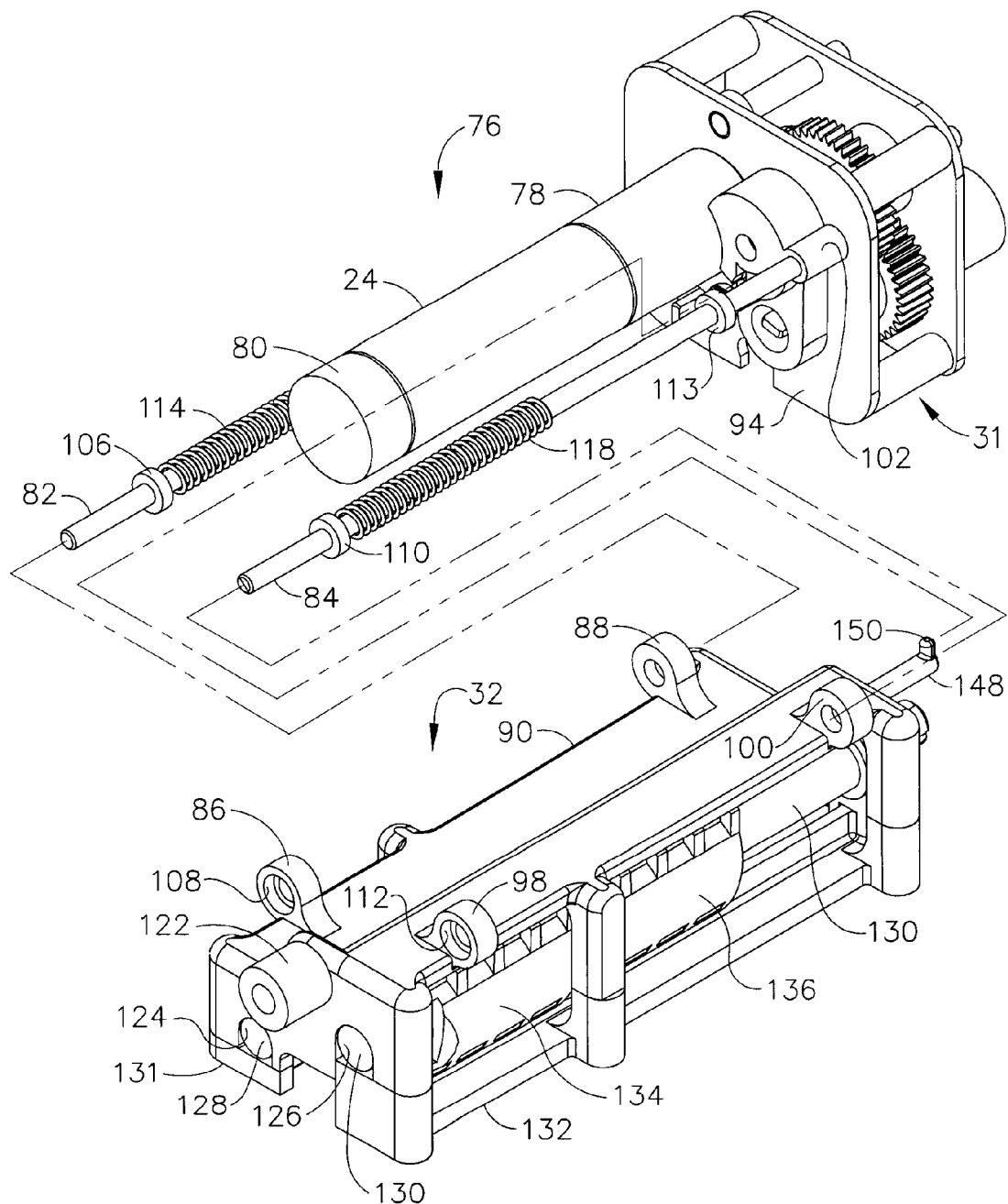
FIG. 4 is an isometric view of the motor drive assembly removed from the carriage frame assembly of FIG. 3.
Figure 5:
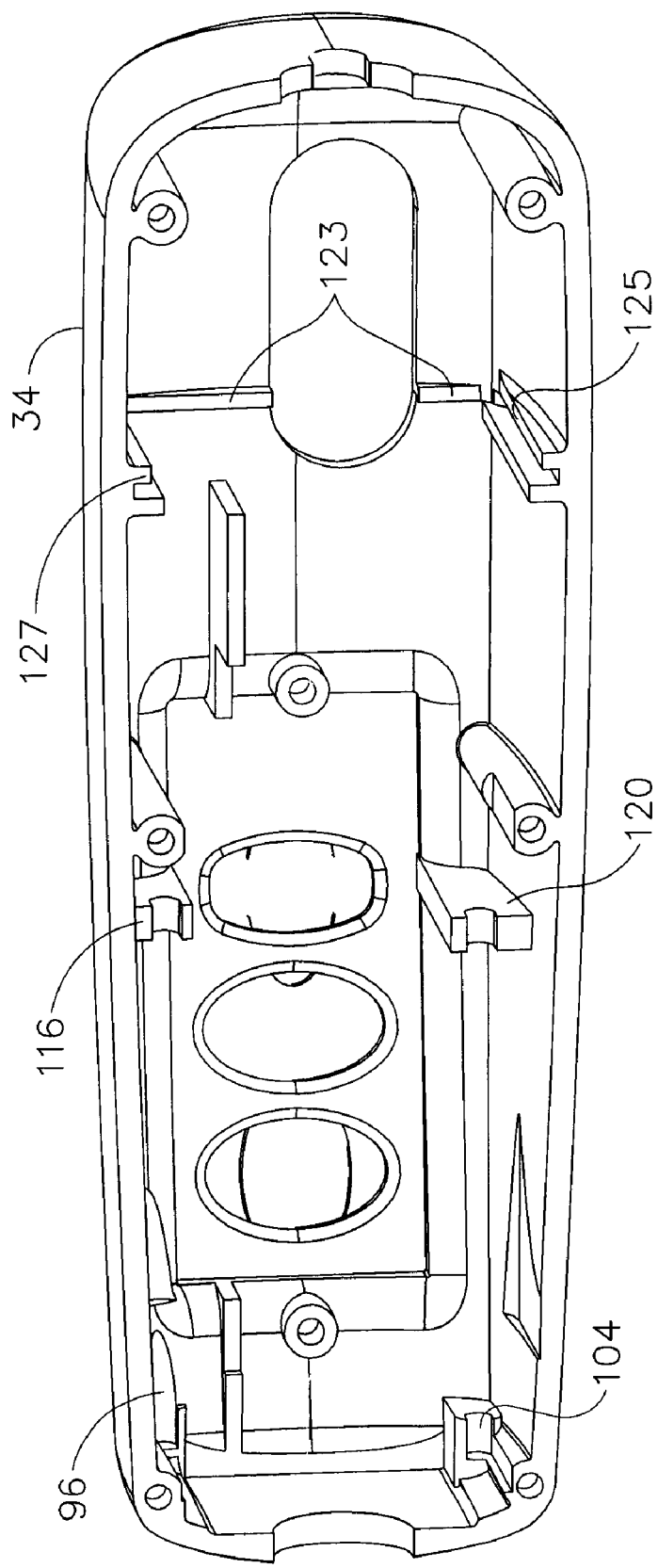
FIG. 5 is a bottom isometric view of the top cover of the reusable handpiece of FIG. 2.

In FIGS. 3-5, a forward projecting cylindrical resilient member 122 fastened to the upper frame 90 reduces noise by contacting the front interior of the top cover 34 slowing distal movement of the carriage frame assembly 32 prior to reaching full travel. The distal bulkhead 94 is restrained by being proximal to a top ridge 123, a right ridge 125, and a left ridge 127 (FIG. 5) formed in the interior of the top cover 34 and to a bottom ridge 129 formed on an upper surface of the lower handle tray 16.

Figure 6:
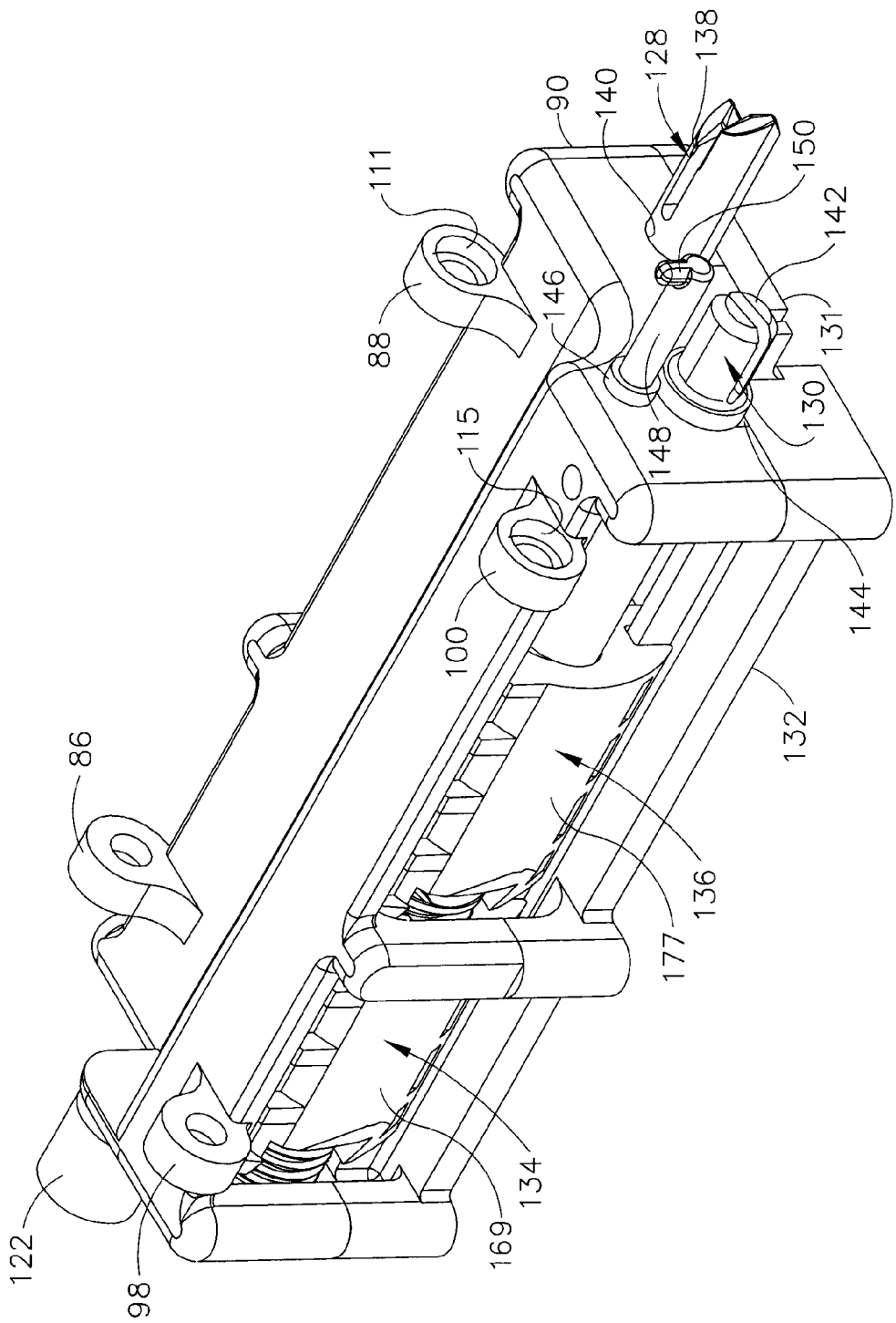
FIG. 6 is a top, left and aft isometric view of the carriage frame assembly of FIG. 4.
Figure 7:
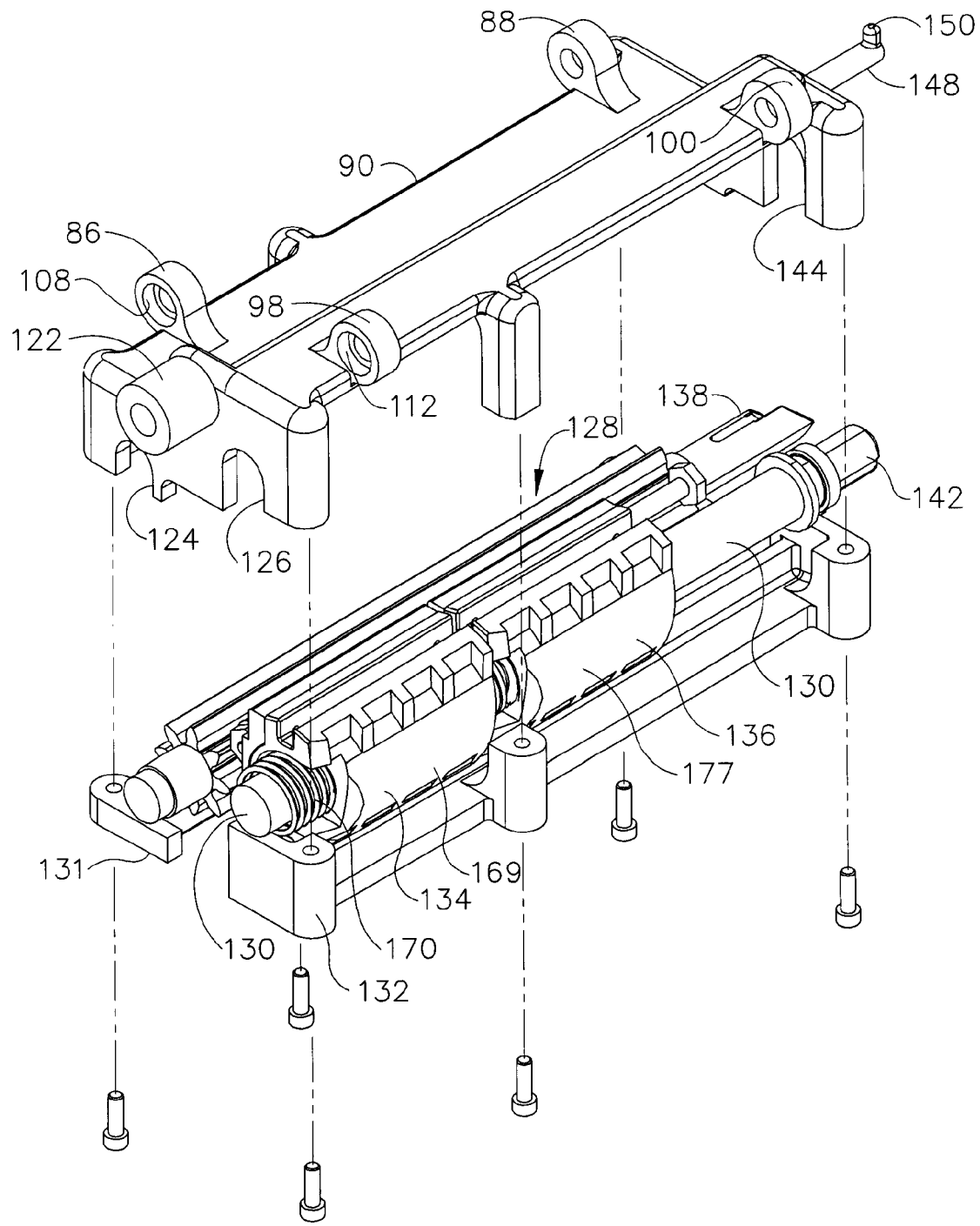
FIG. 7 is a top, left and forward view of the carriage frame assembly of FIG. 4 with an upper frame disassembled.

Returning to FIGS. 3-4 and 7, the upper frame 90 has right and left front shaft apertures 124, 126 that respectfully receive for rotation a distal end of a rotation shaft 128 and a translation shaft 130. The right front shaft aperture 124 is closed by the front portion of a right lower frame 131 of the carriage frame assembly 32. The left front shaft aperture 126 is closed by the front portion of a left lower frame 132 of the carriage frame assembly 32. A front (cutter) carriage 134 and an aft (straw) carriage 136 are received on the translation shaft 130 and are encompassed by the upper and lower frames 90, 132. In FIG. 6, a proximal beveled and slotted end 138 of the rotation shaft 128 extends out of right aft shaft aperture 140 formed in the upper frame 90 for engagement to the transmission section 31 and is closed by an aft portion of the right lower frame 131. A proximal slotted end 142 of the translation shaft 130 extends out of a left aft aperture 144 formed in the upper frame 90 for engagement to the transmission section 31 and is closed by the lower frame 132. A threaded receptacle 146 on the aft end of the upper frame 90 receives a proximally projecting bolt 148 having an upwardly directed strike pin 148 at its proximal end.

Figure 8:
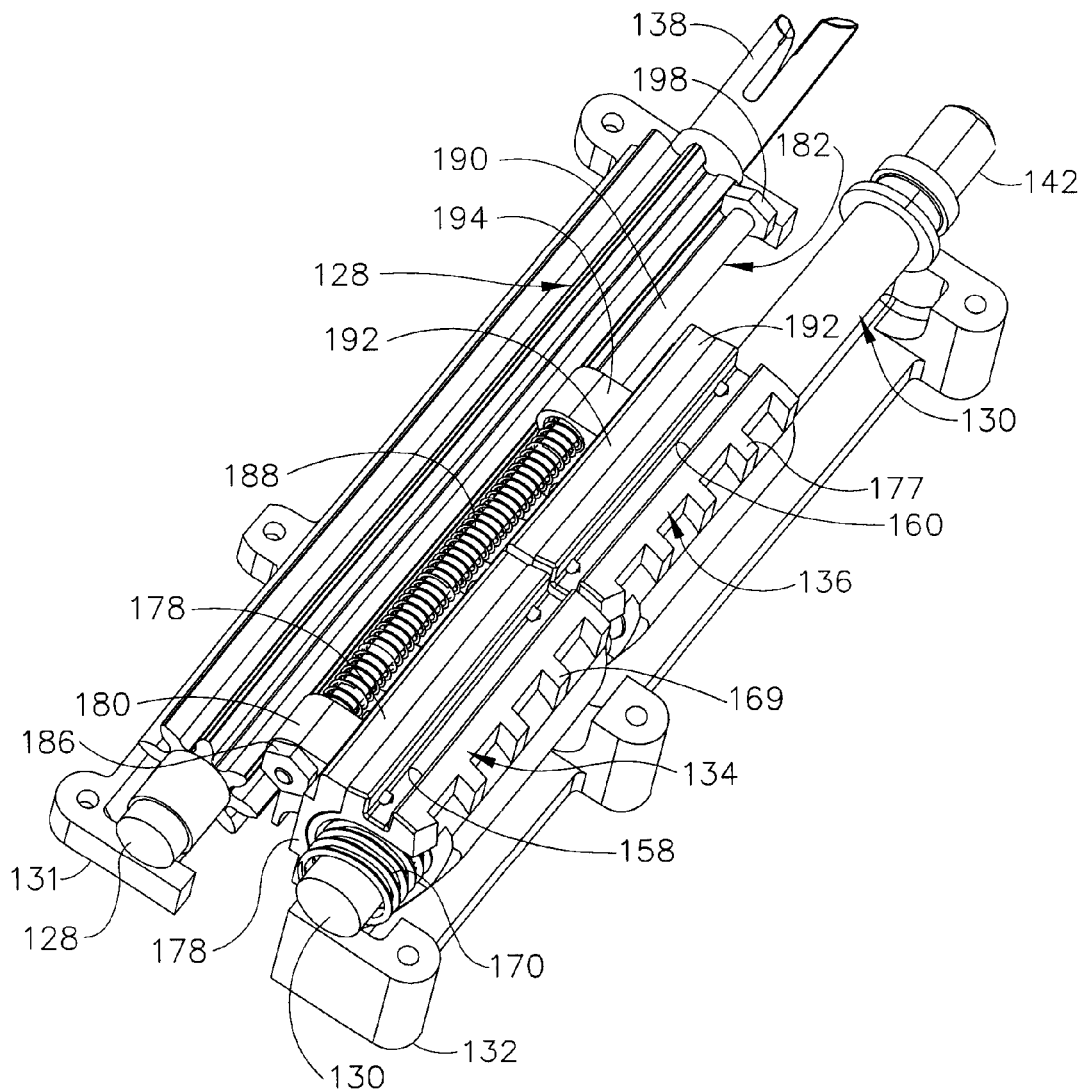
FIG. 8 is a top, left and front isometric view of the carriage frame assembly of FIG. 4 with the upper frame removed.
Figure 9:
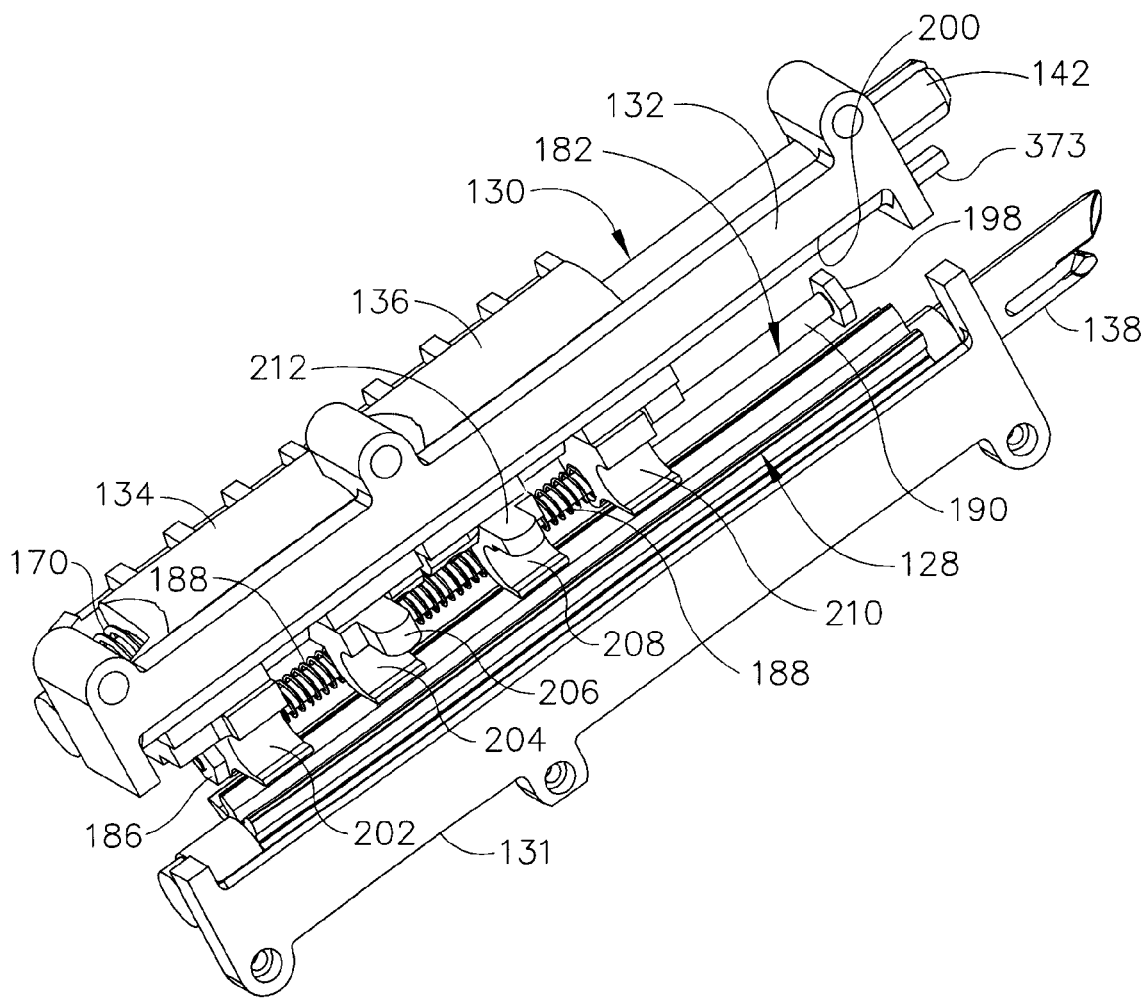
FIG. 9 is a bottom isometric view of the carriage frame assembly of FIG. 8 with the upper frame removed.
Figure 10:
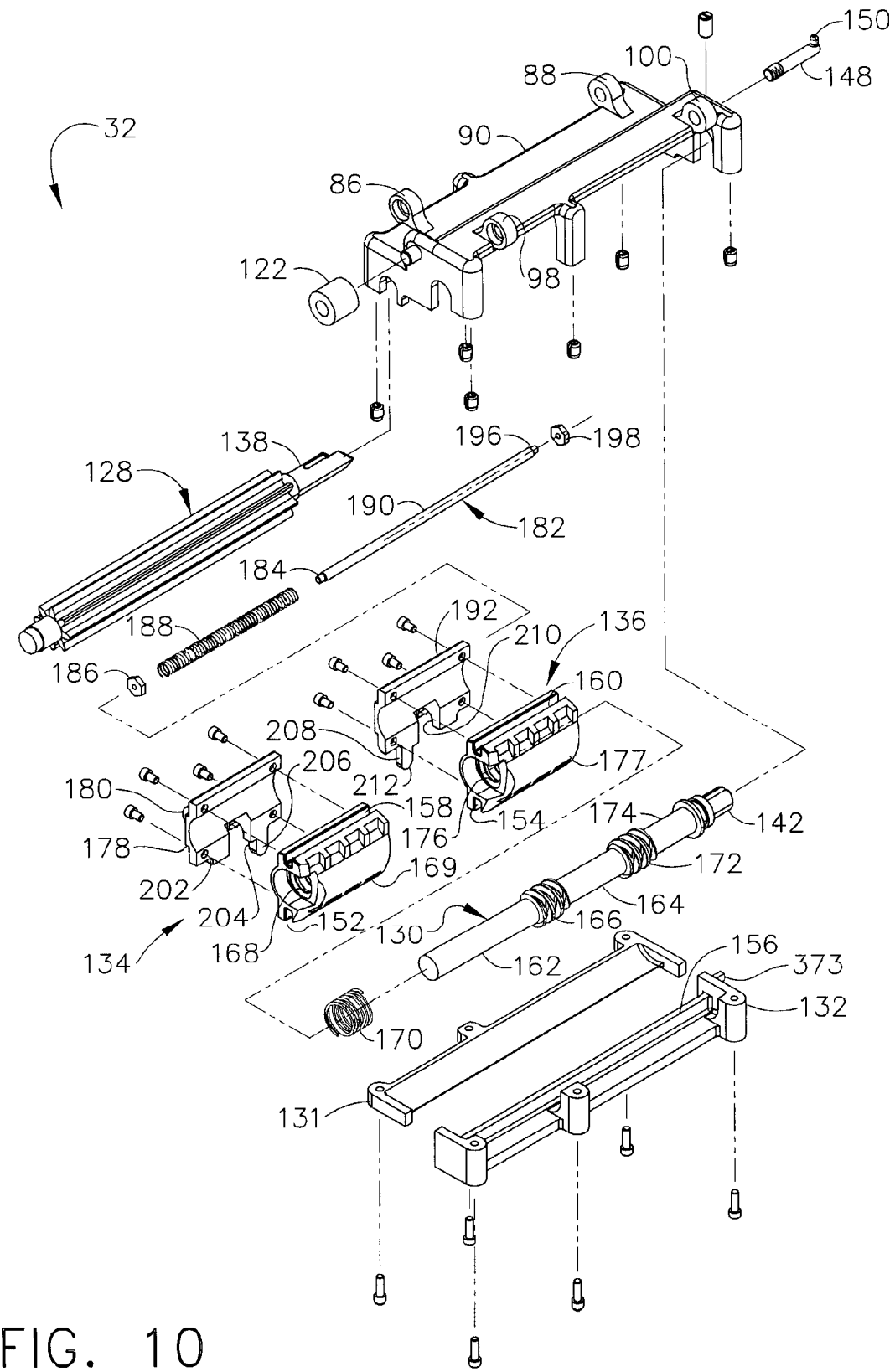
FIG. 10 is a top, left and front isometric exploded view of the carriage frame assembly of FIG. 4.

In FIGS. 7-10, the carriage frame assembly 32 sequences translation of the front and aft carriages 134, 136. With particular reference to FIG. 10, the front and aft carriages 134, 136 respectively include lower longitudinal grooves 152, 154 that slide upon a lower rail 156 upwardly presented on the left lower frame 132. The front and aft carriages 134, 136 respectively include an upper longitudinal groove 158, 160 that slides upon a rail (not shown) downwardly presented on the upper frame 90. The translation shaft 130 has a distal overrun portion 162 and a center overrun portion 164 separated by a front threaded portion 166 that a threaded bore 168 of a front main body portion 169 of the front carriage 134 traverses in response to rotation of the translation shaft 130. A front translation compression spring 170 on the translation shaft 130 distal to the front carriage 134 compresses to allow the front carriage 134 to free wheel when being distally advanced and then biases the front carriage 134 aft to engage the front threaded portion 166 for being retracted upon reversal of rotation of the translation shaft 130.

With particular reference to FIGS. 8 and 10, proximal to the center overrun portion 164 is an aft threaded portion 172 and then a proximal overrun portion 174 that a threaded bore 176 of a back main body portion 177 of the aft carriage 136 traverses in response to rotation of the translation shaft 130 as well as in response to a connection to the front carriage 134. In particular, a front bracket 178 mounted on a right side of the front carriage 134 has a rightward front pin guide 180 that receives a distal end of a longitudinally aligned carriage limiting rod 182. A distal threaded end 184 of the carriage limiting rod 182 extends distally out of the rightward front pin guide 180 and is prevented from backing out by a front nut 186. A long compression spring 188 is received over a shaft 190 of the carriage limiting rod 182 proximal to the rightward front pin guide 180. An aft bracket 192 is attached to a right side of the back main body portion 177 of the aft carriage 136 to extend a rightward aft pin guide 194 that receives the carriage limiting rod 182, which extends a proximal threaded end 196 proximally out of the rightward aft pin guide 194 to receive an aft nut 198 that limits forward movement. The long compression spring 188 biases the aft carriage 136 away from the front carriage 134, delaying retraction of a tissue sample until cutting is complete when full distal translation of the front carriage 134 pulls the aft carriage 136 onto the aft threaded portion 172.

With particular reference to FIG. 9, a lengthwise engagement aperture 200 defined between the right and left lower frames 131, 132 presents engaging structures that actuate the disposable probe assembly 14 and the vacuum syringe assembly 18. The rotation (spur) gear 128 exposes its left side to the lengthwise engagement aperture 200 for engagement with the rotation spur gear section 68 of the cutter gear 62 to impart a rotation. The front bracket 178 has a downward distal half cylinder recess 202 sized to grip the distal reduced diameter bearing surface 64 of the cutter gear 62 (FIG. 2). The front bracket 178 further has a downward proximal half cylinder recess 204 proximally spaced and sized to grip the proximal reduced diameter bearing surface 66 of the cutter gear 62 (FIG. 2) as well as a downwardly projecting front actuation finger 206 to the left side and below of the cutter gear 62 for effecting atmosphere pressure to the probe cannula 22. Similarly, the aft bracket 192 has a downward distal half cylinder recess 208 and a downward proximal half cylinder recess 210 proximally spaced and sized to nonobstructively translate overtop of a tissue retraction tube 211, as well as a downwardly projecting aft actuation finger 212 that selects vacuum pressure for communicating to the probe cannula 22.

Figure 11:
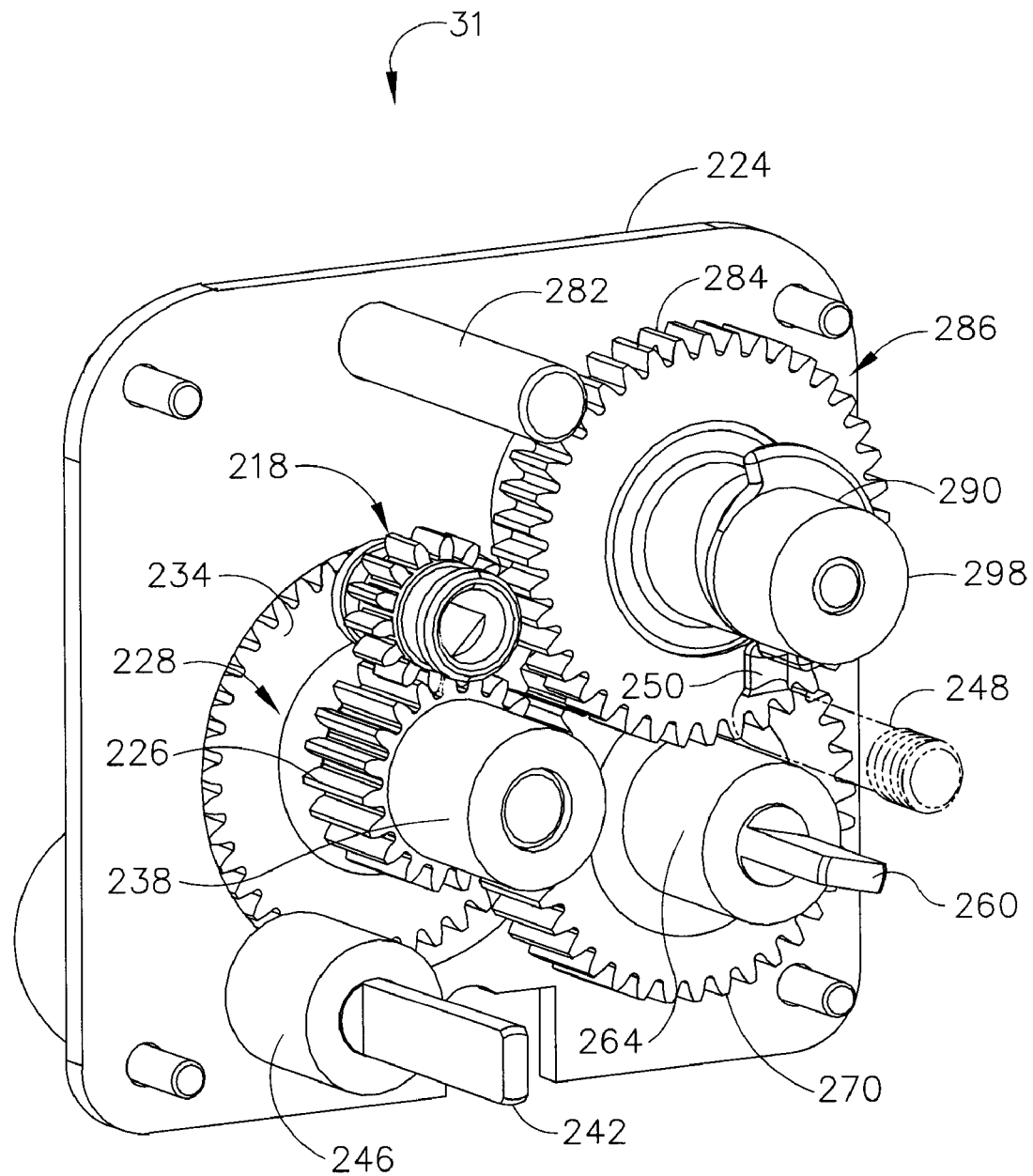
FIG. 11 is a right front view of a transmission section of the motor drive assembly of FIG. 4 with a distal bulkhead removed.
Figure 12:
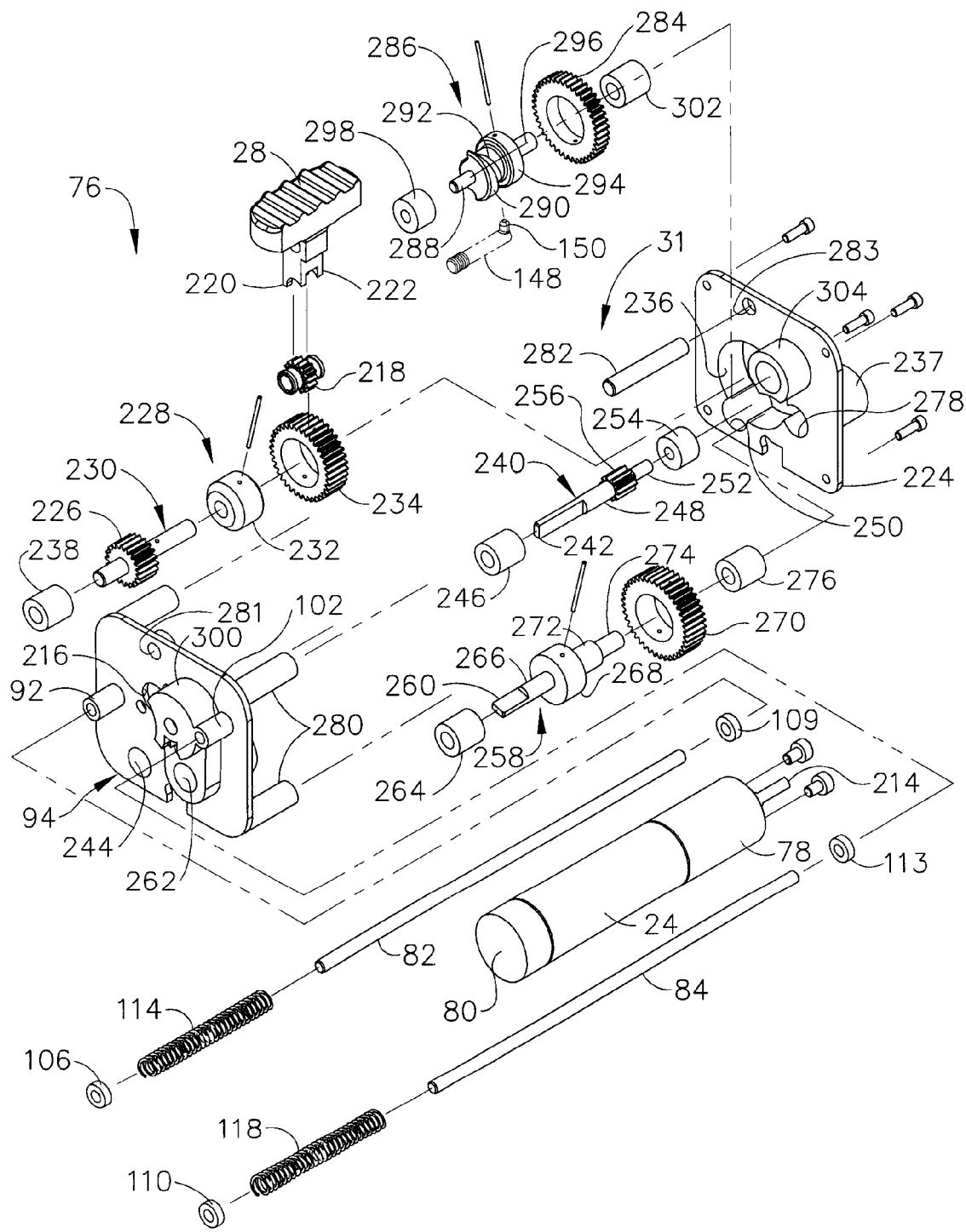
FIG. 12 is a front left exploded view of the transmission section of the motor drive assembly of FIG. 4.

In FIGS. 2-3 and 11-12, the motor drive assembly 76 rotates rotation and translation shafts 128, 130 at a fixed ratio to optimize cutting performance of the cutter tube 36 when the slide button 28 is back. Alternatively, the motor drive assembly 76 imparts a jackhammer vibration to the carriage frame assembly 32 when the slide button 28 is forward. With particular reference to FIGS. 11-12, the planetary gearbox 78 extends proximally to a keyed motor drive shaft 214 (FIG. 12) through a drive shaft hole 216 formed in the distal bulkhead 94. A slide spur gear 218 is received upon the keyed motor drive shaft 214 which remains engaged for rotation between a first distal (jack hammer) position and a second proximal (translation) position in accordance with a position of the slide button 28 whose distal and proximal feet 220, 222 straddle the slide spur gear 218. In FIG. 11, the slide spur gear 218 is close to a proximal bulkhead 224 of the transmission section 31, engaging a small spur 226 of a multiplier gear assembly 228. The multiplier gear assembly 228 includes a longitudinal shaft 230 centrally attached to the small spur gear 226. Proximal thereto, a cylindrical hub 232 is pinned to the longitudinal shaft 230 and in turn is encompassed by and pinned to a large spur gear 234 that rotates within a correspondingly sized, distally open recess 236 formed in proximally projecting container 237 integral to the proximal bulkhead 224. A front cylinder bearing 238 received on a distal portion of the longitudinal shaft 230 is received by the proximal surface of the distal bulkhead 94.

A first output drive shaft 240 distally presents a right angle prismatic end 242 shaped to engage the beveled and slotted end 138 of the rotation shaft 128 that passes through a lower right hole 244 in the distal bulkhead 94. A cylindrical spacer 246 is received over a distal cylindrical portion 248 of the first output shaft 240, taking up the space between the rotation shaft 128 and the proximal bulkhead 224. A distally open recess 250, formed as part of the container 237 that communicates from below with the recess 236, is shaped to receive a proximal cylindrical end 252 of the first output drive shaft 240 and encompasses cylindrical bearing 254 as well as a small spur gear segment 256, which is distal thereto and engages the large spur gear 234 of the multiplier gear assembly 228.

A second output drive shaft 258 distally presents a right angle prismatic end 260 to engage the proximal slotted end 142 of the translation shaft 130 that extends through a low left hole 262 in the distal bulkhead 94. A cylindrical spacer 264 is received over a distal cylindrical portion 266 of the second output drive shaft 258 proximal to the right angle prismatic end 260 and distal to a wider diameter hub segment 268 that is encompassed by and pinned to a large spur gear 270 that engages the small spur gear 226 of the multiplier gear assembly 228. Proximal to the hub segment 268 is a wide spacer segment 272 and then a narrow cylindrical end 274 that receives a cylindrical bearing 276 that resides within a correspondingly-sized, distally open recess 278 that communicates from the left with the recess 236 and is formed as part of the same container 237.

The distal and proximal bulkheads 94, 224 are structurally attached to one another in parallel alignment traverse to the longitudinal axis of the biopsy device 10 by cylindrical legs 280 molded to and proximally projecting from rectangular corners of the distal bulkhead 94 and fastened to the proximal bulkhead 224. In addition, a pin 282 passes through holes 281, 283 longitudinally aligned in the distal and proximal bulkheads 94, 224 respectively along a top surface.

When the slide button 28 is moved distally to the jackhammer position, the sliding spur gear 218 disengages from the small spur gear 226 and engages a large spur gear 284 of a rotary camming gear assembly 286. A camming shaft 286 from distal to proximal includes a distal cylindrical end 288, a cam wheel 290, a mid-shaft portion 292 that receives the upwardly directed strike pin 150 of the proximally projecting bolt 148, a wide diameter hub 294 that is encompassed by and pinned to the large spur gear 284, and a proximal cylindrical end 296. A distal cylindrical bearing 298 is received within a proximally open container 300 projecting distally from the distal bulkhead 94 and in turn receives the distal cylindrical end 288 of the camming shaft 286. A proximal cylindrical bearing 302 is received within a distally projecting and open cylinder 304 formed on the proximal bulkhead 224 and in turn receives the proximal cylindrical end 296 of the camming shaft 286.

As the camming shaft 286 rotates clockwise as viewed from behind, the cam wheel 290 presents a proximal surface to the distal edge of the strike pin 150 that is more proximal until the interrupted portion of the camming wheel 290 is presented, allowing the strike pin 150 to return to a distal position under the urging of the distal biasing of the right and left compression springs 114, 118.

Figure 13:
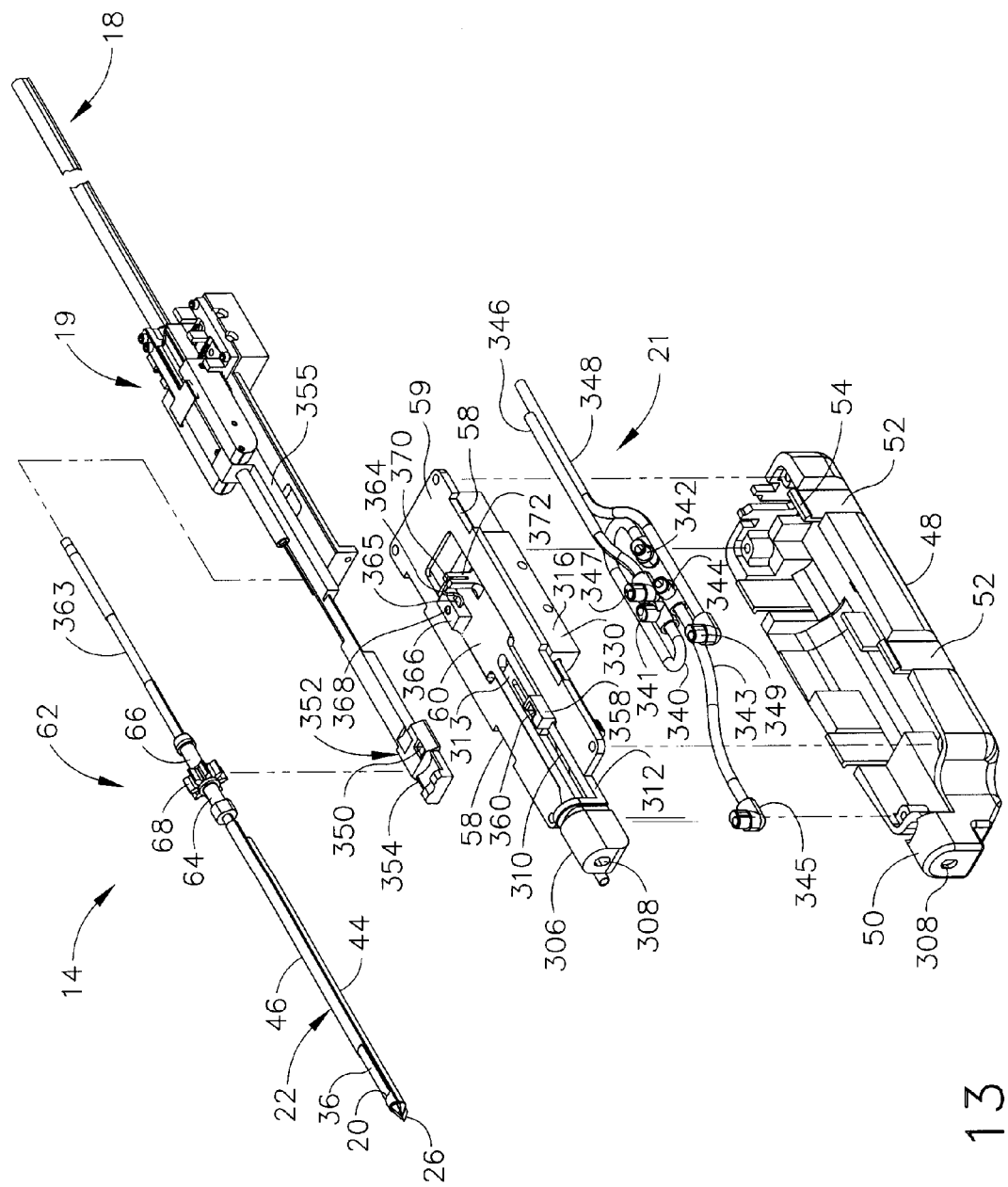
FIG. 13 is a left front isometric view of the disposable probe assembly of FIG. 1 with a hand-held distal portion partially disassembled from the serial tissue stacking assembly.
Figure 14:
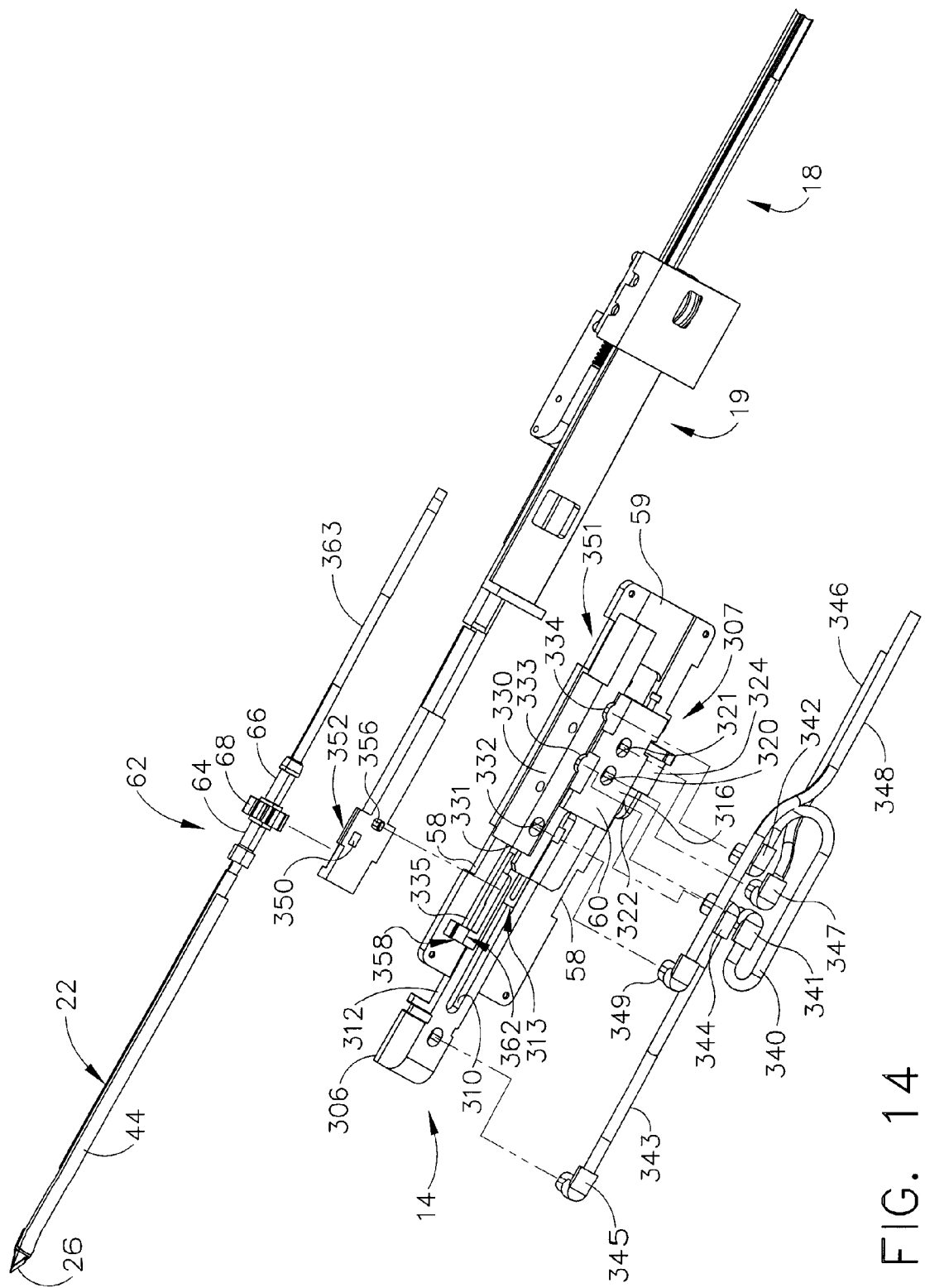
FIG. 14 is an isometric view from below and to the left of the hand-held distal portion of the disposable probe assembly of FIG. 13 with the cover components omitted.
Figure 15:
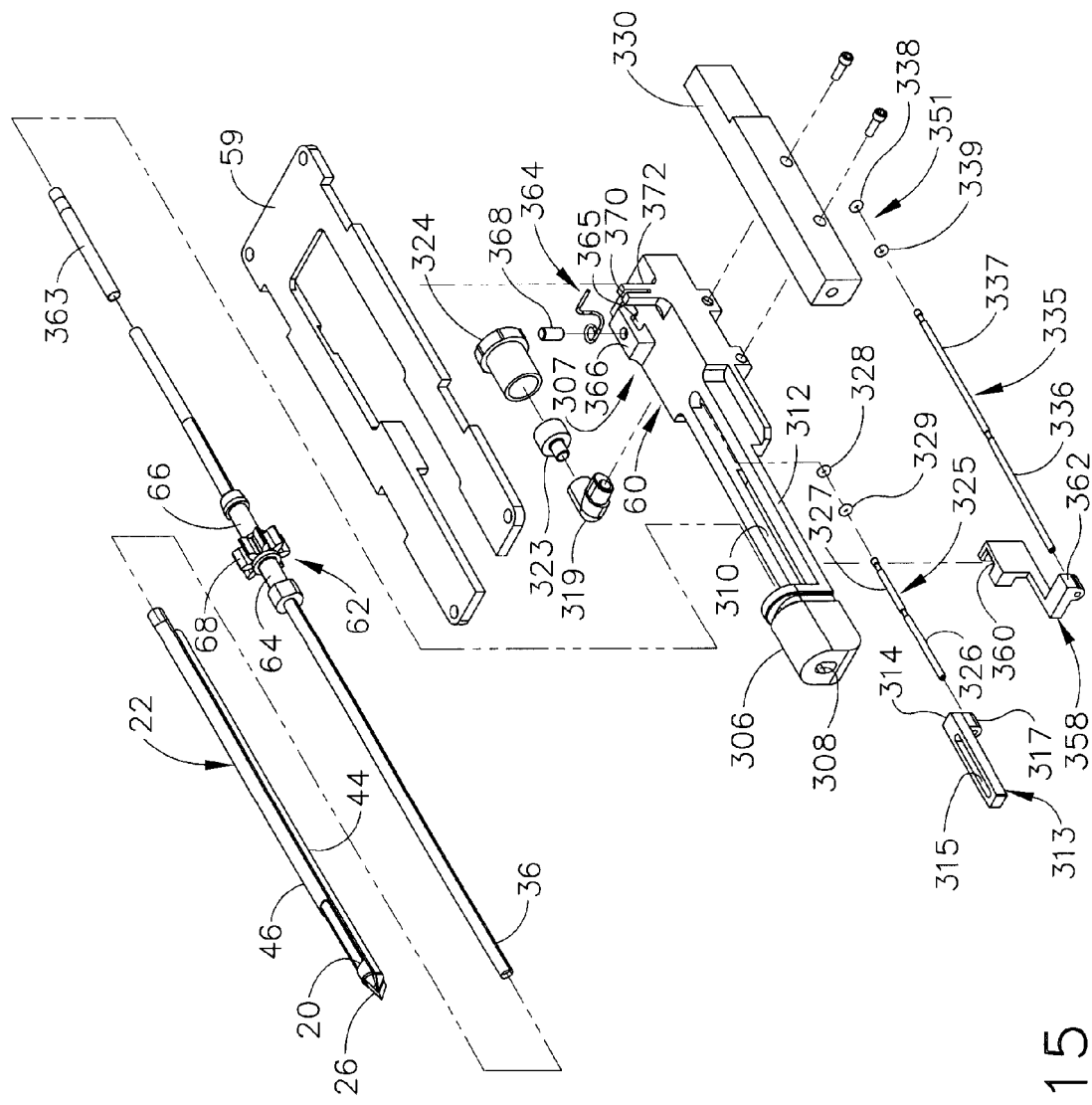
FIG. 15 is an isometric view of an exploded portion of the disposable probe assembly.

DISPOSABLE PROBE ASSEMBLY. In FIGS. 13-28, the disposable probe assembly 14 has movable components that respond to the actuating motions of the reusable handpiece 12. With particular reference to FIGS. 13-15, the distal portion 21 of disposable probe assembly 14 includes the probe cannula 22 that is supported by the probe support body 60. The probe support body 60 includes a distal probe mount 306 that is received within the distal probe mount cover 50 of the bottom cover 48. The front carriage 134 (FIG. 9) controls a vacuum valve 307. In particular, proximal to and underlying a longitudinal axis of the disposable probe assembly 14 defined by a probe guide hole 308 passing through the distal probe mount 306, a vertically open longitudinal trough 310 is formed into a necked portion 312 of the probe support body 60. A cutter carriage-driven vacuum valve driver 313 has an elongate driver body 314 (FIG. 15) that longitudinally translates within the longitudinal trough 310 and upwardly presents an elongate slot 315 for being indirectly moved by the downwardly projecting front actuation finger 206 of the front carriage 136 (FIG. 9).

With particular reference to FIGS. 13-15, a proximal block portion 316 is attached to the necked portion 312 of the probe support body 60. A lower mounting 317 (FIG. 15) extending from the elongate driver body 314 distal to and longitudinally aligned with a distally open, longitudinally aligned vacuum valve bore 318 (FIG. 22) is formed in the proximal block portion 316 of the probe support body 60. Central and proximal ports 320, 321 (FIG. 14) communicate with the vacuum valve bore 318 from an underside of the proximal block portion 316 and a distal port 322 communicates laterally from a right side of the proximal block portion 316. A right distal 90-degree fitting 319 communicates between the distal port 322 and an intake filter 323 within an outer hose fitting 324.

Figure 25:
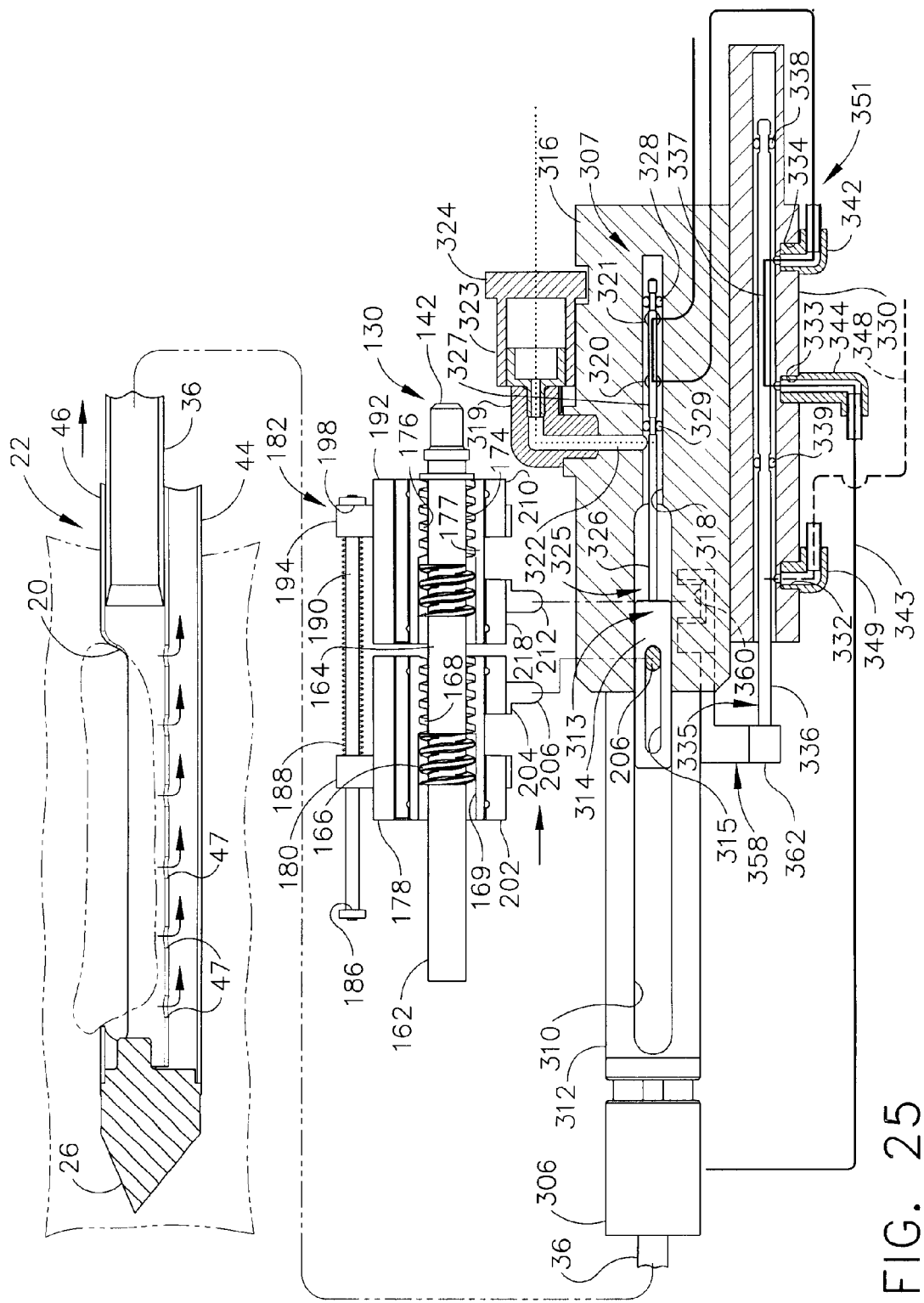
FIG. 25 is a diagrammatic view of the hand-held distal portion of the disposable probe assembly of FIG. 1 with both carriages retracted supplying vacuum pressure to the side aperture to prolapse tissue into the probe cannula.

A vacuum valve control rod 325 has a distal actuating portion 326 extending distally out of the valve bore 318 with a distal end positionable under the downwardly open portion of the longitudinal trough 310 and attached to the lower mounting 317 of the vacuum valve driver 313. The vacuum valve control rod 325 also has a valve spool portion 327 that longitudinally translates within the valve bore 318 to selectively position between a first position and a second position. A proximal O-ring 328 near a proximal end of the valve spool portion 327 and a distal O-ring 329 are spaced such that the first position entails the O-rings 328, 329 bracketing the central and distal ports 320, 322 (FIG. 22) and the second position entails the O-rings 328, 329 bracketing the proximal and central ports 321, 320, respectively (FIG. 25).

The aft carriage 136 controls an air valve 351. In particular, an air valve body 330 is attached to a left side of the proximal block portion 316 and includes a distally open longitudinal air valve bore 331 (FIG. 22) depicted in FIG. 14 as accessed by a distal left port 332, a left center port 333, and a left proximal port 334. An air valve control rod 335 has a distal actuating portion 336 extending distally out of the air valve bore 331. The valve control rod 335 also has a valve spool portion 337 that longitudinally translates within the air valve bore 331 to selectively position between a first position and a second position. A proximal O-ring 338 near a proximal end of the valve spool portion 337 and a distal O-ring 339 are spaced such that the first position entails the O-rings 338, 339 bracketing the central and distal ports 333, 332 and the second position entails the O-rings 338, 339 bracketing the proximal and central ports 334, 333, respectively.

A valve connecting vacuum conduit 340 has one end attached to a lower center ninety-degree fitting 341 attached to the central port 320 of the vacuum valve bore 318 and the other end attached to an aft left ninety-degree fitting 342 that communicates with the left proximal port 334 of the air valve bore 331. A distal conduit 343 is attached at one end to a center ninety-degree fitting 344 that communicates with the left center port 333 and at the other end at a probe union ninety-degree fitting 345 that communicates with the lateral lumen 44. A vacuum supply conduit 346 is attached at one end to a distal ninety-degree fitting 347 that communicates with the proximal port 321 and at the other end to a vacuum supply (not shown). An air supply conduit 348 is attached at one end to a distal ninety-degree fitting 349 that communicates with the distal left port 332 and the other end to an air supply (not shown).

The front actuation finger 206 of the front carriage 136 (FIGS. 9-10) is received within an upwardly open socket 350 formed on a left side of a cutter carriage-driven indexing shuttle 352 having a lateral concave recessed band 354 shaped to encompass with a clearance a lower portion of the rotation spur gear section 68 of the cutter gear 62. An indexing arm 355 proximally attached to the indexing shuttle 352. In FIG. 14, a downwardly projecting vacuum actuator lug 356 attached to an underside of the indexing shuttle 352 is received within the elongate slot 315 of the vacuum valve driver 314 to selectively communicate the vacuum supply to the probe cannula 22. An air shuttle 358 longitudinally rides on a left edge of the necked portion 312 of the probe support body 60 and upwardly projects an air valve tab socket 360 positioned to receive the aft actuating finger 212 of the aft carriage 138 (FIG. 9). A downward mounting arm 362 of the air shuttle 358 is attached to the distal actuating portion 336 of the air valve control rod 335 extending distally out of the air valve bore 331.

A straw hook wire 364 supports a midpoint of a sample retraction tube 363 in place upon the probe support body 60 prior to engagement with the reusable handpiece 12. A curled lower right end passes into leftwardly opening 365 along the top right surface of the proximal block portion 316 of the probe support body 60 into a small mounting block 366 extending upwardly from a right side with a downwardly inserted pin 368 passing through the curled lower right end to hold the straw hook wire 364 in place. The straw hook wire 364 has a horizontal portion attached to the curled end that passes under the sample retraction tube 363, bending upward and then bending leftward and horizontally again through a lateral slot 370 in a vertical wire support member 372 formed onto a left side of the top surface of the proximal block portion 316. It should be appreciated that engagement of the reusable handpiece 12 deflects the left portion of the straw hook wire 364. This facilitates commonality with disposable probe assemblies in which the straw hook wire 364 keeps a translating sample retraction straw in place prior to mounting to the reusable handpiece 12 (not shown).

350 as a rib feature 373 (FIG. 9) deflects the left portion of the straw hook wire 364. This facilitates commonality with disposable probe assemblies in which the straw hook wire 364 keeps a translating sample retraction straw in place prior to mounting to the reusable handpiece 12 (not shown).

Figure 20:
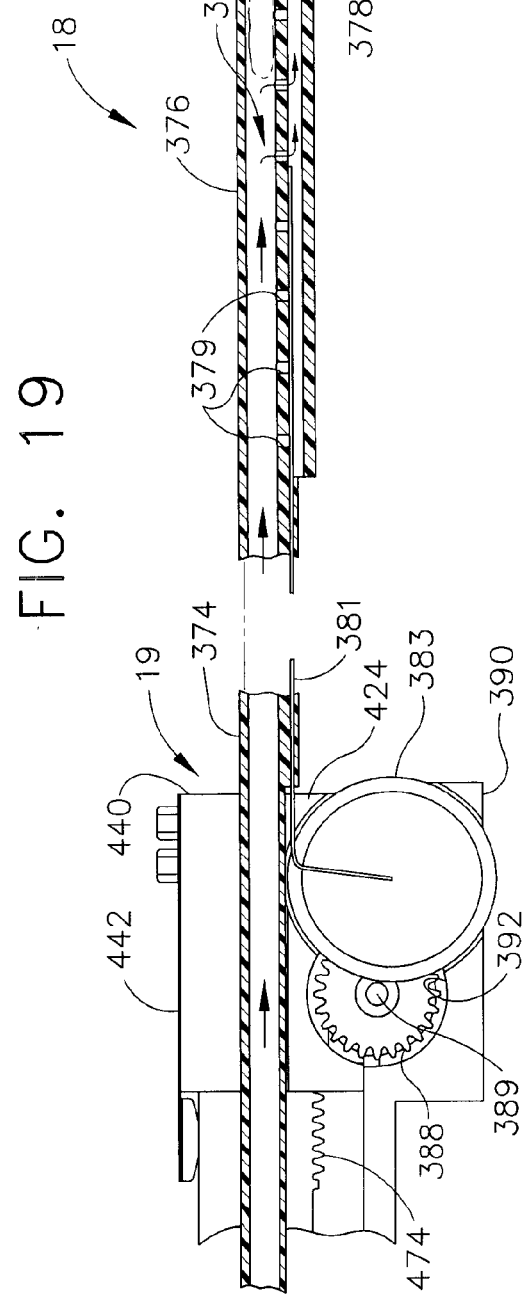
FIG. 20 is a left side view in longitudinal vertical cross section through the serial tissue stacking assembly of FIG. 1 as the additional tissue sample is stacked against a previous sample and a sample vacuum tape is drawn distally to expose additional internal vacuum holes for the next tissue storage location.
Figure 21:
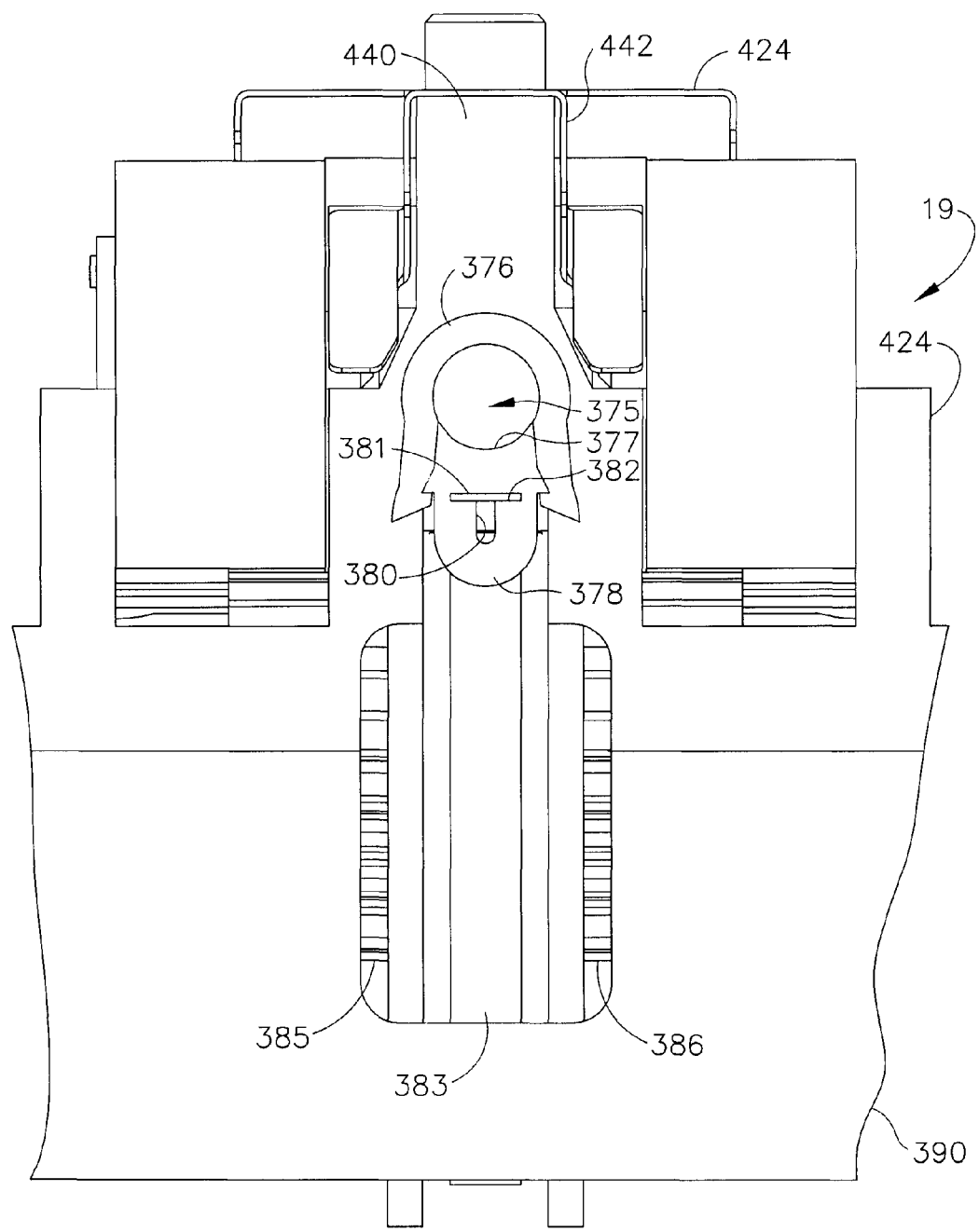
FIG. 21 is an aft view in elevation of the serial tissue stacking assembly of FIG. 1.

With particular reference to FIGS. 16 and 19-21, the serial tissue stacking assembly 18 includes a connecting sample straw 374 that passes through the indexing assembly 19 to mate with the sample retraction tube 363 (FIG. 15). A tissue storage lumen 375 that proximally communicates with the connecting sample straw 374 is formed by an inverted U-cross section elongate flexible cover 376 attached along its bottom edges as depicted especially in FIG. 21 to a perforated top surface 377 of a proximal vacuum tube 378. A longitudinally aligned series of internal vacuum holes 379 that pass between the tissue storage lumen 375 and a proximal vacuum lumen 380 defined within the proximal vacuum tube 378 are selectively blocked by a sample vacuum tape 381 that is inserted from a distal side into a horizontal slot 382 (FIG. 21) that interrupts vacuum holes 379 from communicating from the top surface 377 to the underlying vacuum lumen 380 of the proximal vacuum tube 378. As the tissue storage lumen 375 fills with tissue samples from a proximal end, the vacuum tape 381 may be drawn distally to expose vacuum holes 379 just distal to the last stacked tissue sample (FIG. 20). Thereby, the tissue storage and proximal vacuum lumens 375, 380 remain in pneumatic communication with an incoming tissue sample drawn fully proximally into proximity to the last tissue sample.

Figure 16:
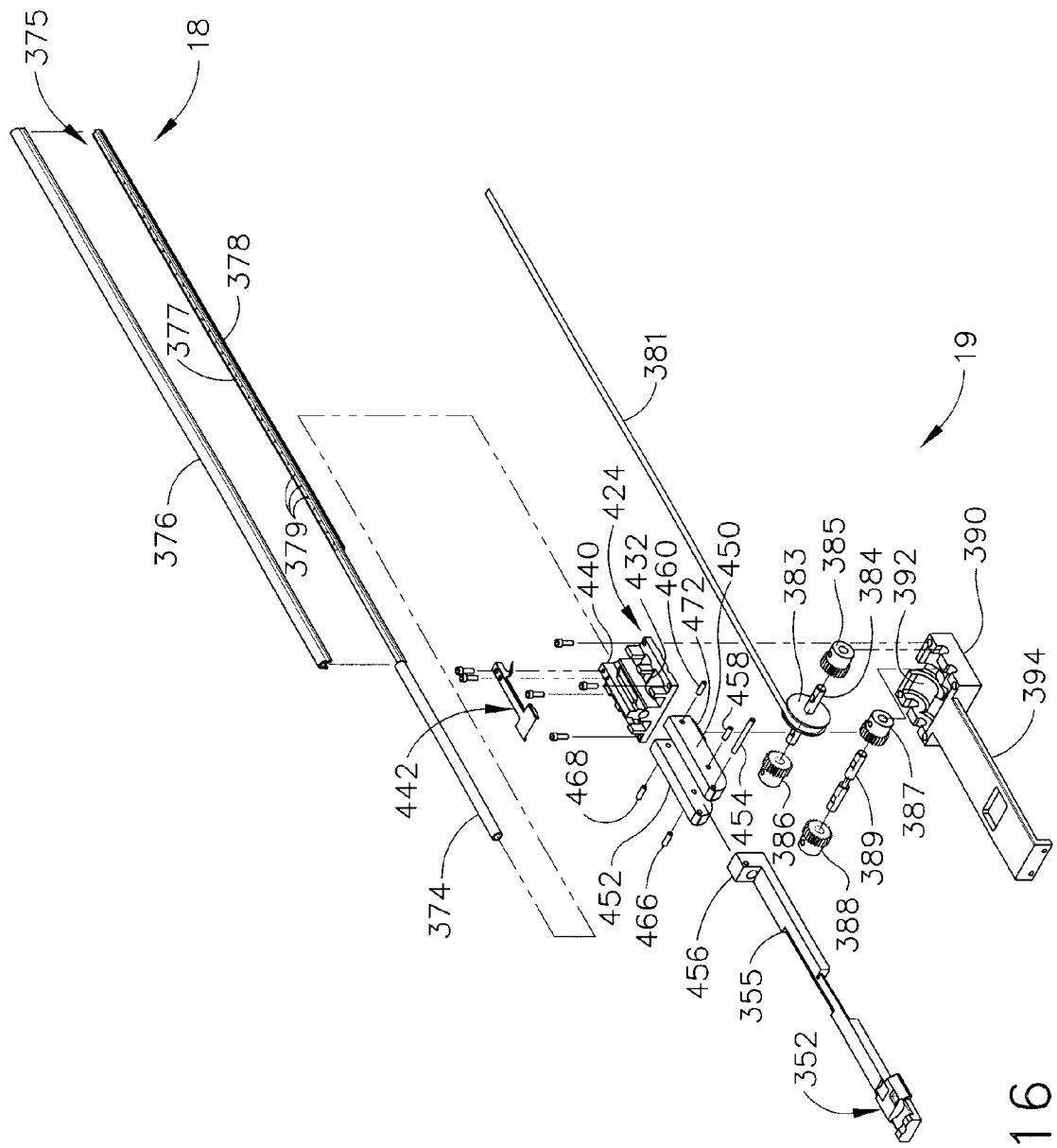
FIG. 16 is an isometric exploded view of the serial tissue stacking assembly of FIG. 1.

With particular reference to FIG. 16, the indexing assembly 19 draws the vacuum tape 381 distally by rotating top forward a transversely aligned tape wheel 383 in response to reciprocating movement of the indexing arm 355. The tape wheel 383 is a spool that is turned by a tape wheel axle 384 that is attached for rotation on lateral sides to flanking left and right tape drive gears 385, 386. Left and right index gears 387, 388 are engaged respectively to distal faces of the left and right tape drive gears 385, 386 and rotate on an index axle 389 that is horizontally parallel and distally spaced from the tape wheel axle 384. An index base 390 has a base recess 392 shaped to support the lower half of each end of the axles 384, 389 and to encompass a lower half of the gears 385-388, and tape wheel 383.

Figure 17:
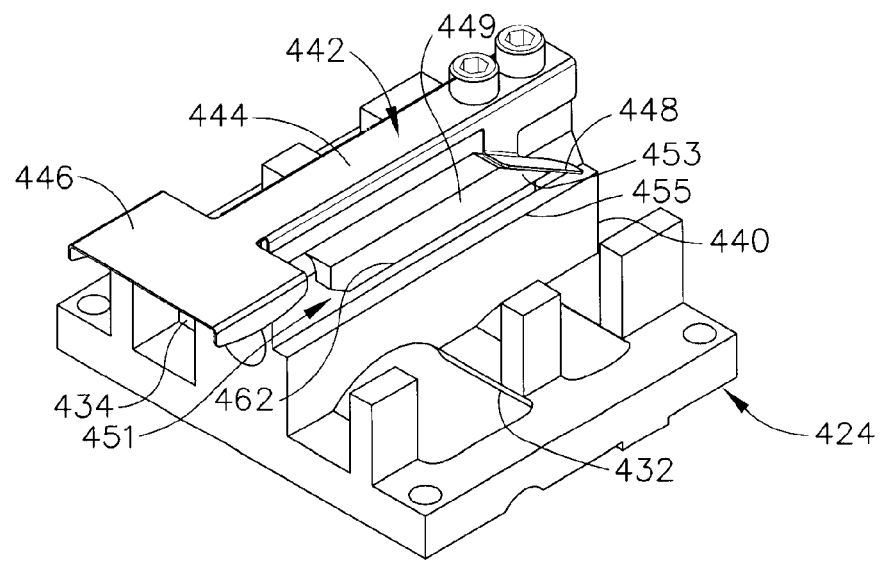
FIG. 17 is an isometric detail view of an indexer gear cover of the serial tissue stacking assembly of FIG. 16.

In FIG. 17, a top indexer gear cover 424 mounts overtop of the index base 390 and contacts a top half of each end of the axles 384, 389. The top indexer gear cover 424 encompasses a top half of the left and right index gears 387, 388 except for the exposure through distally open left and right vertical slots 432, 434. In FIGS. 16-17, a central beam 440 defined between the left and right vertical slots 432, 434 has a T-shaped hold down spring 442 mounted on top with its narrow end 444 mounted to a proximal end of the central beam 440. A laterally wider end 446 extends laterally overtop but not distally forward of both vertical slots 432, 434. A cyclic spring gate 448 extends laterally to the left and right from a proximal end of the T-shaped hold down spring 442 and ramps downwardly and proximally.

With particular reference to FIG. 17, each side of the central beam 440 has a respective left and right lower pin guide 462, formed as an upper surface of a wider lower portion 455. An upper pin guide 449 extends laterally out from the central beam 440 on each side and is spaced respectively above the lower pin guides 462 to form a lower pin channel 451. Although only the left upper pin guide 449 is depicted, it should be appreciated that the right side includes a mirror image upper pin guide. A rear ramped portion 453 of the upper pin guide 449 underlies and supports the cyclic spring gate 448.

In FIG. 16, left and right cyclic arms 450, 452 have distal ends mounted on respective ends of a transverse cyclic axle 454 whose central portion passes through an upturned proximal end 456 of the index arm 355. Left fore and aft cyclic pins 458, 460 extend rightward out of the left cyclic arm 450. Right fore and aft cyclic pins 466, 468 extend leftward out of the right cyclic arm 452. Each cyclic arm 450, 452 includes a respective left and right bottom rack segment 472, 474 close to the distal rotating end positioned to engage a respective index gear 387, 388 under the downward urging of the laterally wider distal end 446 of the T-shaped hold spring 442.

Figure 18A:
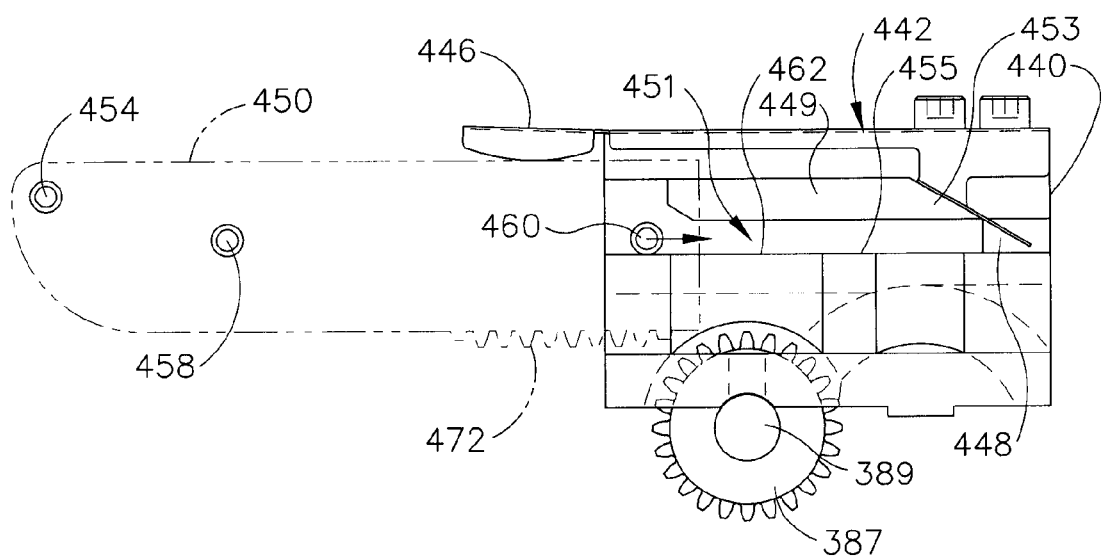
FIG. 18A is a left side diagrammatic view of a left cyclic arm shown in phantom down for engagement during proximal stroke engaged to the indexer gear cover of FIG. 17.
Figure 18B:
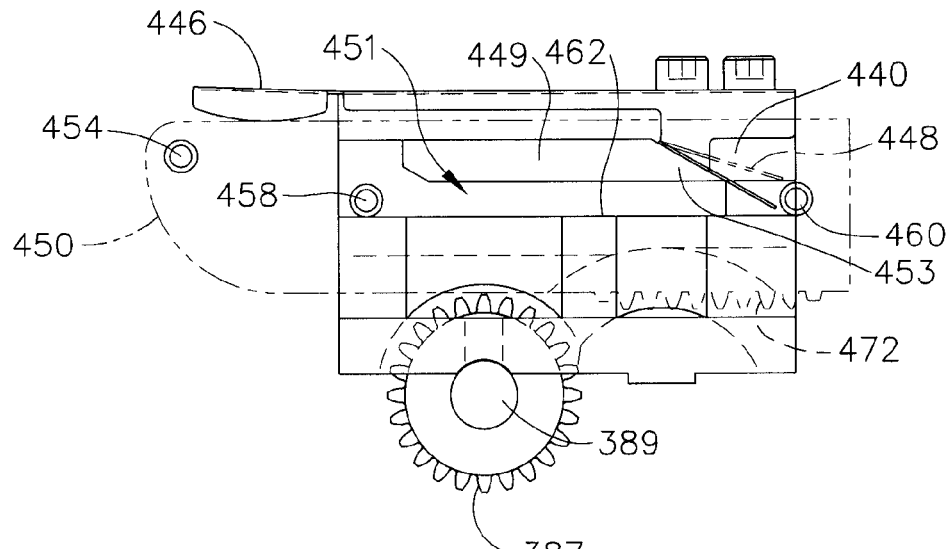
FIG. 18B is a left side diagrammatic view of the left cyclic arm shown in phantom at a proximal most position on the indexer gear cover of FIG. 17.
Figure 18C:
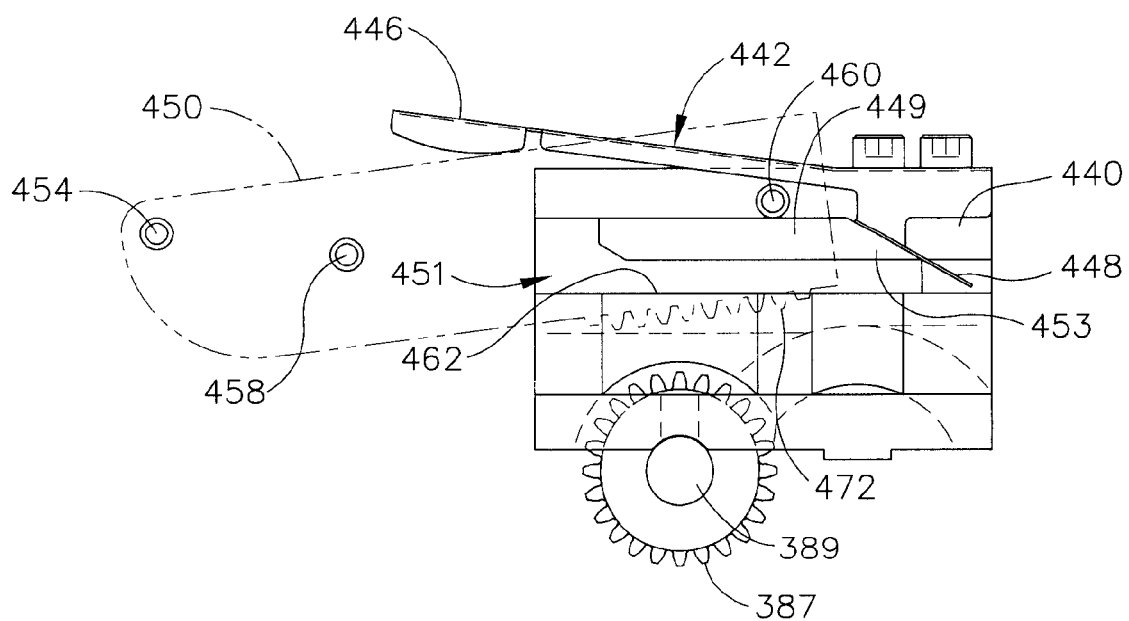
FIG. 18C is a left side diagrammatic view of the left cyclic arm shown in phantom during a return distal stroke rotated upward for disengagement.
Figure 19:
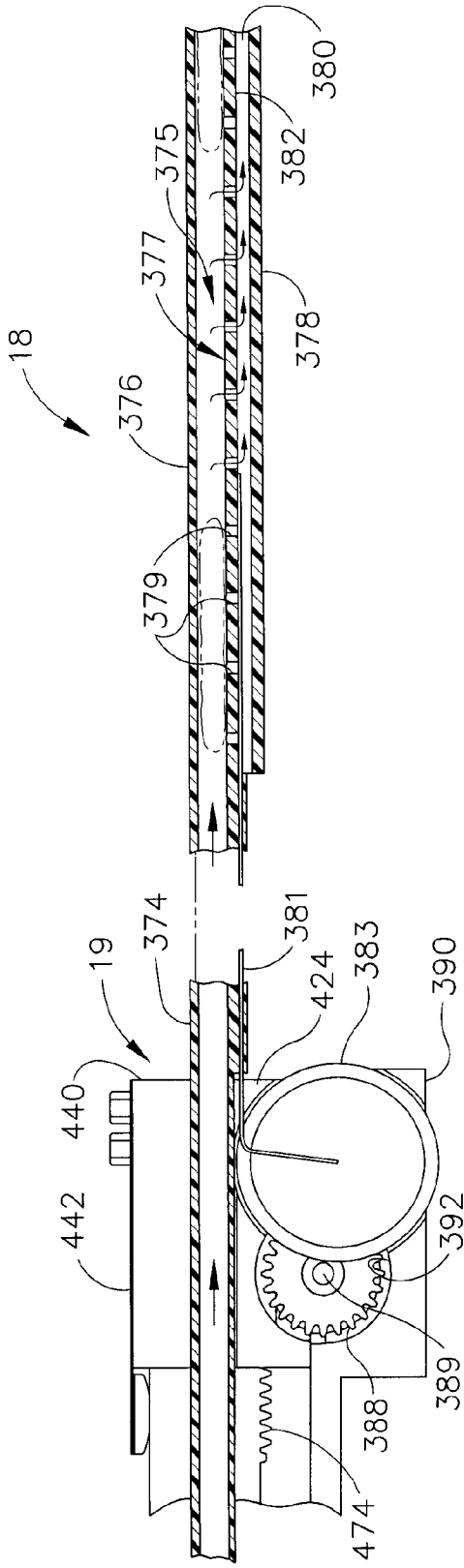
FIG. 19 is a left side view in longitudinal vertical cross section through the serial tissue stacking assembly of FIG. 1 as an additional tissue sample is proximally retracted into a tissue storage lumen.

With reference to FIG. 1, the left and right cyclic arms 450, 452 are at their distal most positions. It should be appreciated that the left and right aft cyclic pins 460, 468 are distal to respective upper pin guides 449. In FIG. 18A, proximal movement of the left cyclic arm 450 presents the rack segment 472 to rotate the left index gear 387 (subsequent to depiction in FIG. 18A) top aft, held in engagement by the T-shaped hold down spring 442. Proximal movement of the cyclic arms 450, 452 causes the left and right index gear 387, 388 to rotate top aft, which in turn causes the left and right tape drive gears 385, 386 and the tape wheel 383 top forward, thus drawing the vacuum tape 381 distally. In FIG. 18B, the left cyclic arm 450 has reached its proximal most position, wherein the left aft pin 460 has pushed through the cyclic spring gate 448 and out of the lower pin channel 451. In FIG. 18C, upon distal movement of the left cyclic arm 450, the left aft pin 460 rides up the cyclic spring gate 448, rotating the right cyclic arm 450 out of engagement with the left index gear 387. It should be appreciated that the left aft pin 460 will drop off of the front of the upper pin guide 449 as the distal most position is reached and be positioned to enter again the lower pin channel 451 under the downward urging of the T-shaped hold down spring 442 to its initial position to repeat the cycle.

Figure 22:
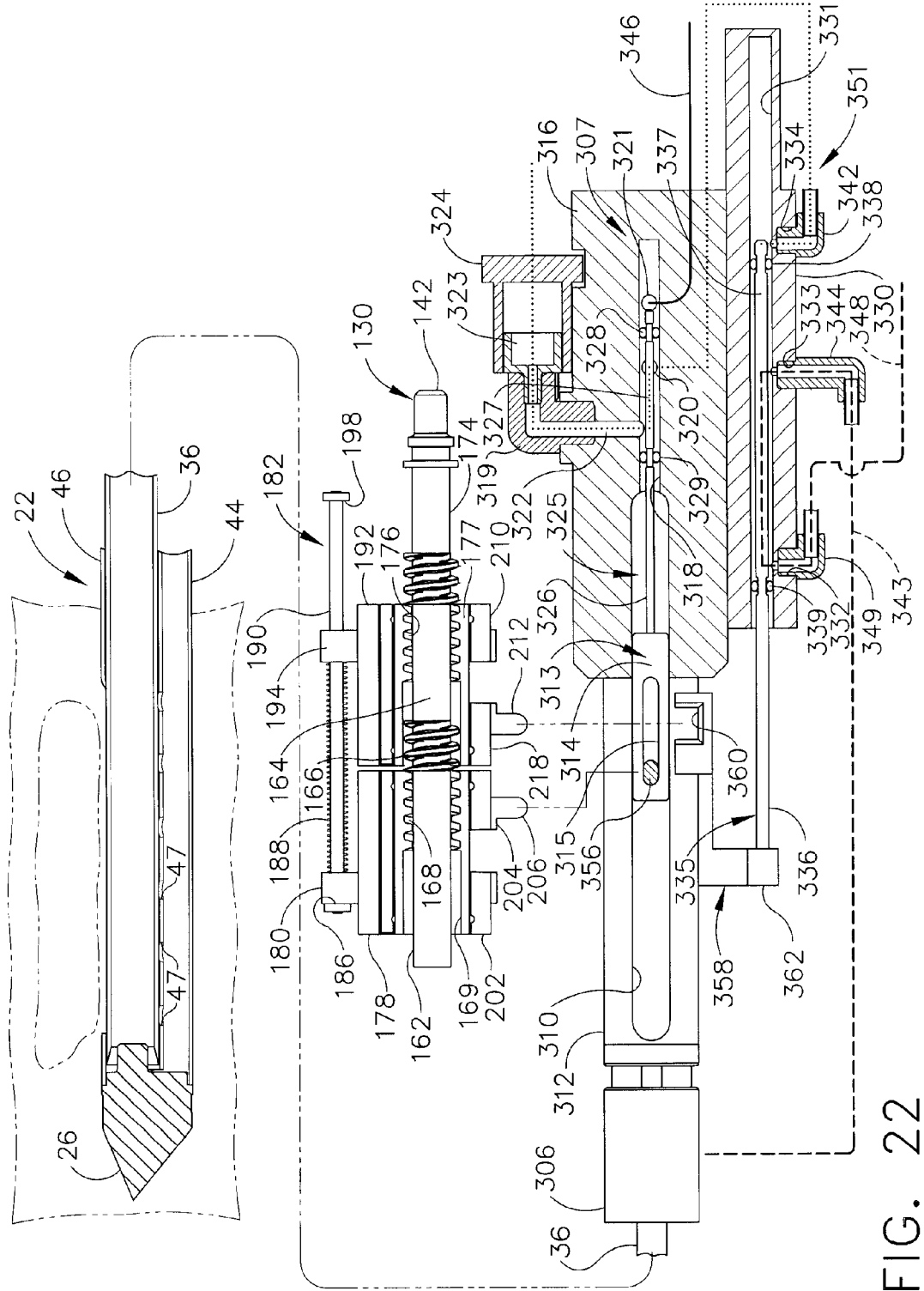
FIG. 22 is diagrammatic view of the hand-held distal portion of the disposable probe assembly of FIG. 1 with both carriages advanced for closing a side aperture in a probe cannula for insertion into tissue.

In FIGS. 22-28, the operation of the reusable handpiece 12 and the hand-held distal portion 21 of the disposable probe assembly 14 are depicted sequentially in diagrammatic form to illustrate how the tape indexing assembly 19 and serial tissue stacking assembly 18 are operated in conjunction with the taking of vacuum assisted core biopsy samples. In FIG. 22, the hand-held distal portion 21 of the disposable probe assembly 14 has both carriages 134, 136 distally advanced in an initial state for closing the side aperture 20 in the probe cannula 22 for insertion into tissue. The front carriage 134 also advances the cutter carriage-driven vacuum valve driver 313 to its distal position, switching the vacuum valve 307 distally to provide atmospheric pressure to the air valve 351 (i.e., atmosphere in distal port 322 and out center port 320 to left proximal port 334). The aft carriage 136 positions the air valve 351 to shut off the input from the vacuum valve 307, instead causing the air supply conduit 348 to communicate through the left distal port 332 to the left center port 333 to the distal conduit 343 to pressurize the lateral lumen 44.

Figure 23:
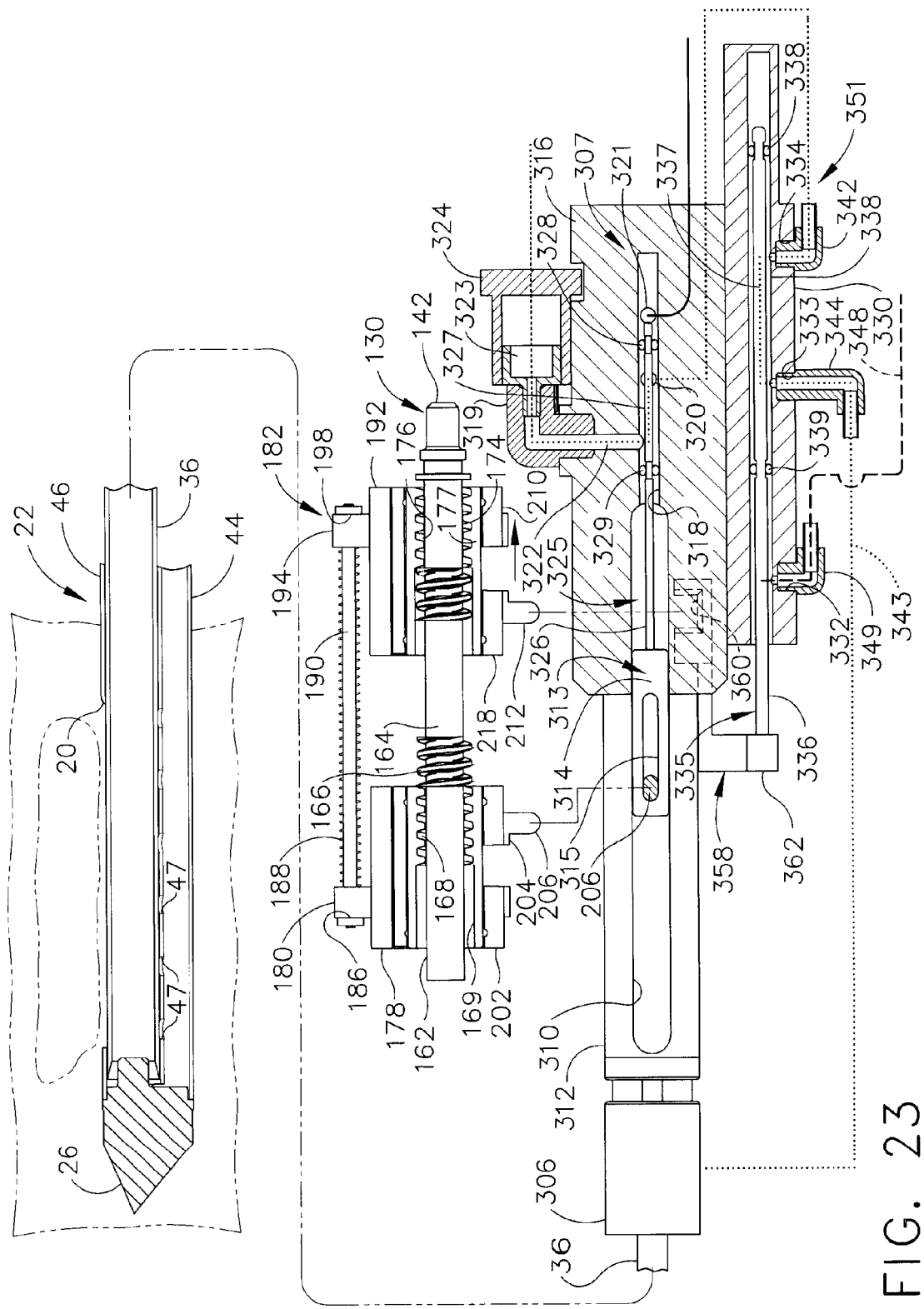
FIG. 23 is a diagrammatic view of the hand-held distal portion of the disposable probe assembly of FIG. 1 with an aft carriage retracted to vent the probe cannula to atmosphere to begin a new sample taking cycle.

In FIG. 23, the aft carriage 136 has proximally retracted, switching the air valve 351 so that the atmosphere pressure provided by the vacuum valve 307 now communicates through the left proximal port 334 to the left center port 334 to the distal conduit 343 to the lateral lumen 44, venting the probe cannula 22 to begin a new sample taking cycle.

Figure 24:
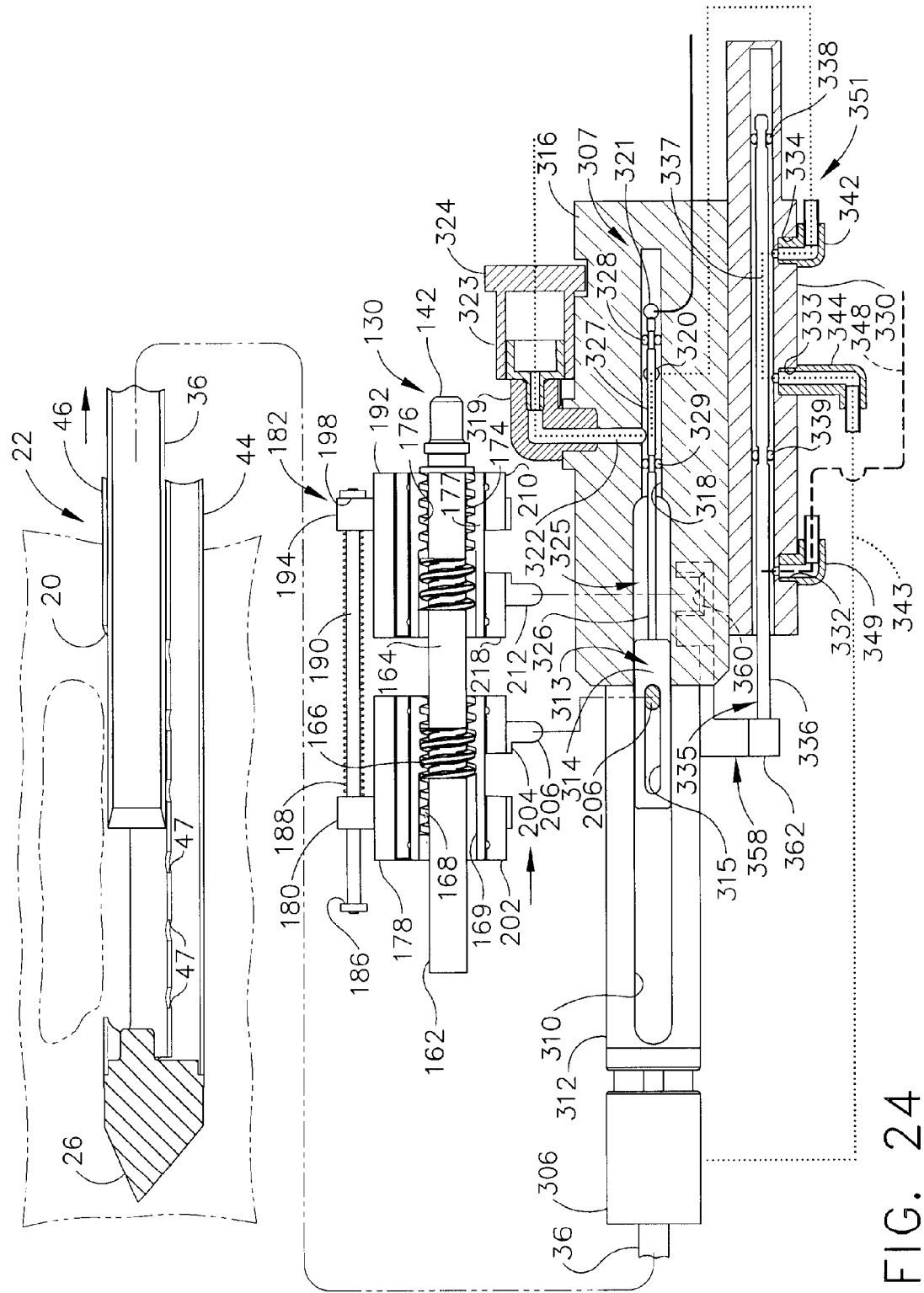
FIG. 24 is a diagrammatic view of the hand-held distal portion of the disposable probe assembly of FIG. 1 with a front carriage beginning to retract, opening the side aperture and beginning to switch to supplying vacuum to the probe cannula.

In FIG. 24, the front carriage 134 has begun to proximally retract while the aft carriage 136 remains at its proximal most position. The cutter tube 36 retracts exposing a portion of the side aperture 20 of the probe cannula 22 while the vacuum and air valves 307, 351 remain in the same state with the probe cannula 22 vented to the atmosphere.

In FIG. 25, the front carriage 134 has reached its proximal most position, fully retracting the cutter tube 36 to expose the side aperture 20 of the probe cannula 22, which is now under vacuum pressure to prolapse tissue by having the front carriage 134 position the vacuum valve 307 to pass vacuum supply from the proximal port 321 through the center port 320 to the left central port 330 to the left distal port 332 to the lateral lumen 44, drawing air through the internal vent holes 47.

Figure 26:
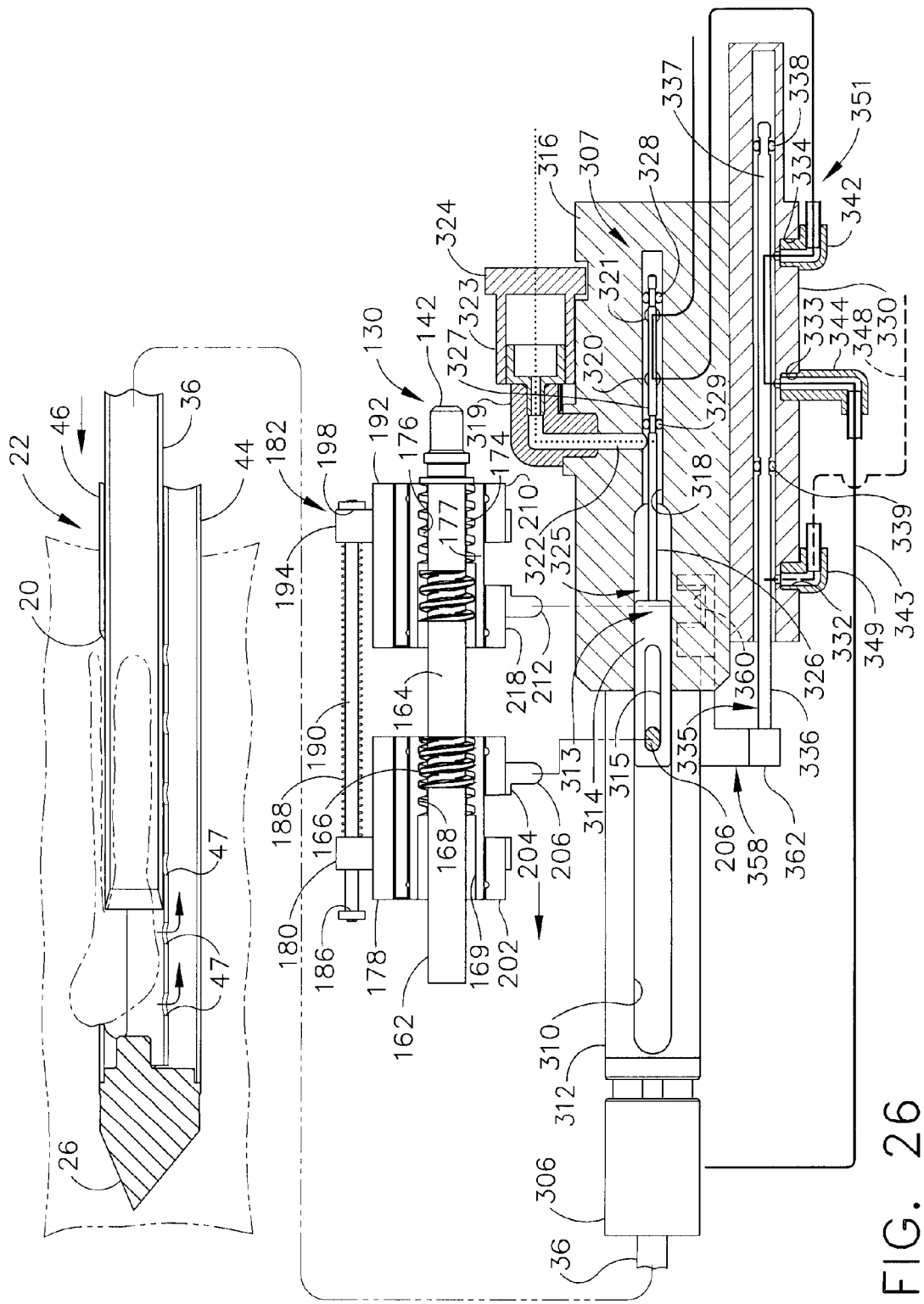
FIG. 26 is a diagrammatic view of the hand-held distal portion of the disposable probe assembly of FIG. 1 with the front carriage being distally advanced to sever tissue.

In FIG. 26, the front carriage 134 has begun to distally advance, severing tissue, while the vacuum valve 307 remains switched to vacuum supply and the air valve 351 remains in the state passing the vacuum pressure through to the lateral lumen 44.

Figure 27:
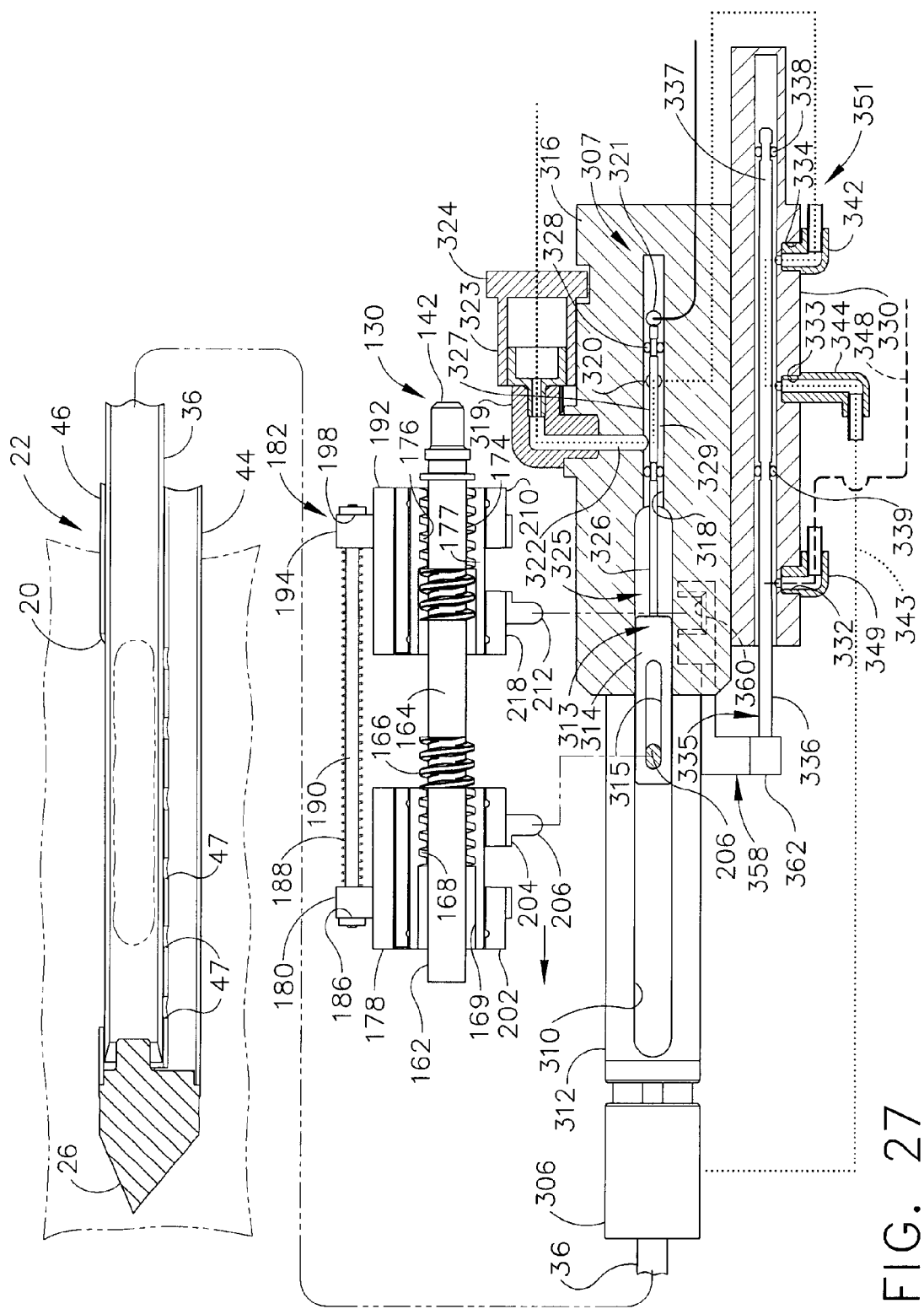
FIG. 27 is a diagrammatic view of the hand-held distal portion of the disposable probe assembly of FIG. 1 with the front carriage fully distally translated to complete severing of a tissue sample with atmosphere pressure supplied to the side aperture through a lateral lumen.

In FIG. 27, the front carriage 134 has been fully distally advanced, causing the cutter tube 36 to completely sever the prolapsed tissue into a tissue sample and switching the vacuum valve 307 to vent to the atmosphere. With the aft carriage 136 still back, the air valve 351 passes the atmosphere pressure to the lateral lumen 44 to vent the probe cannula 46.

Figure 28:
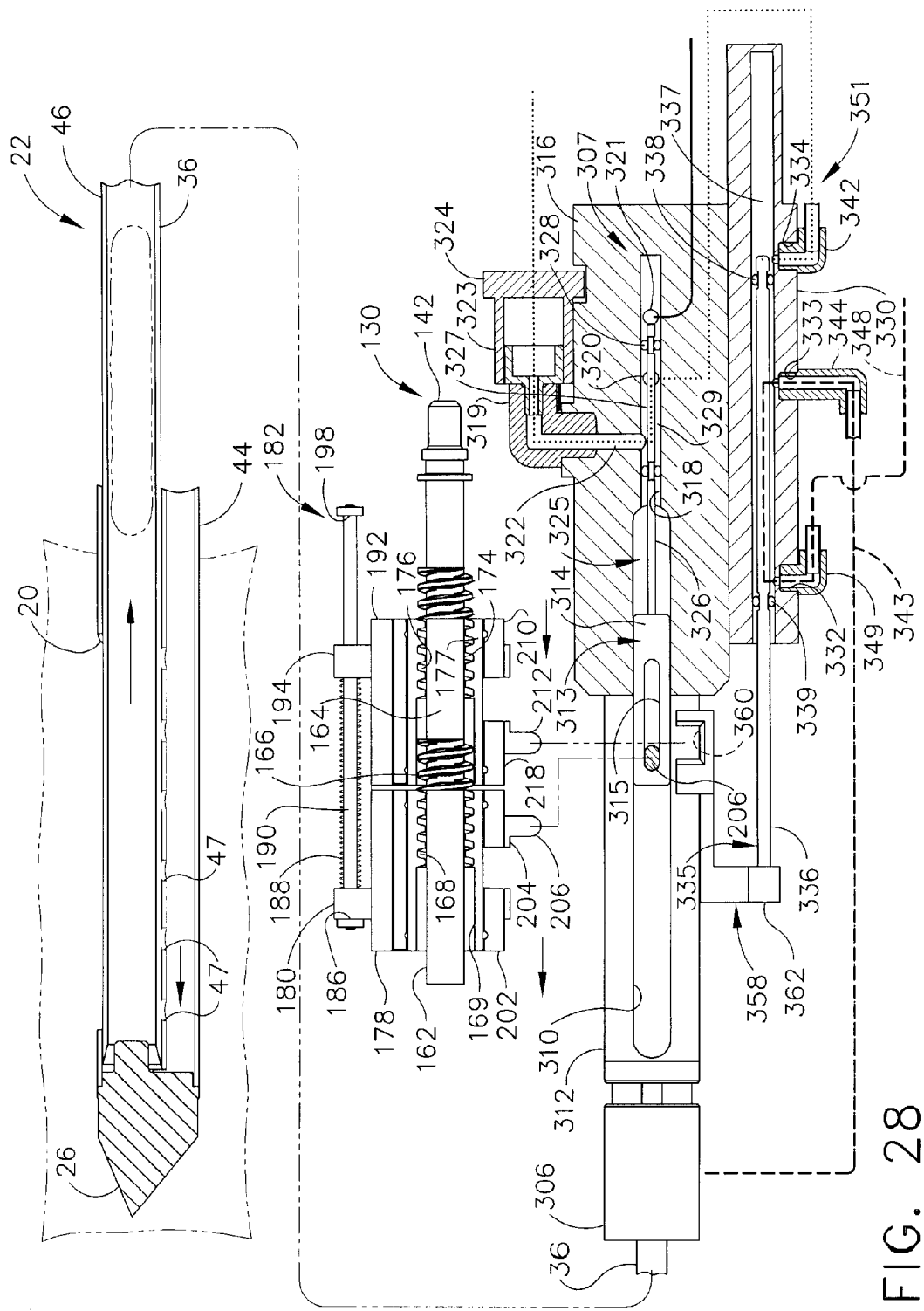
FIG. 28 is a diagrammatic view of the hand-held distal portion of the disposable probe assembly of FIG. 1 with the aft carriage distally advanced to retract the tissue sample with vacuum pressure.

In FIG. 28, the aft carriage 136 has been distally advanced, switching the air valve 351 to pass air pressure front the left distal port 332 to the left center port 333 to the lateral lumen 44. The increased air pressure passes through the holes 47 to the distal end of the cutter lumen 47 causing the tissue sample to be blown proximally back up the cutter tube 36 out of the distal hand-held portion 21 of the biopsy device 10 into the sample cassette assembly 18.

The clinicians benefit from being able to visually or diagnostically image the tissue samples while still being able to maintain the probe cannula 22 in tissue to take additional samples, insert therapeutic agents, deposit a marker, etc. Thus, a minimum of reinsertions and verifications of position are necessary, yet the clinician is reassured that proper samples are being taken. Moreover, avoidance of biohazards is provided by encasing the tissue samples for convenient transport for pathology assessment. Further, the individual storage allows correlating a particular sample taken at a specific position in the patient's breast. In addition, the apparatus is portable with a minimum of needed interconnections.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While preferred embodiments of the present invention have been shown and described herein, it will be obvious to those skilled in the art, given the benefit of the present disclosure, that such embodiments are provided by way of example only. Numerous variations, changes, and substitutions will now occur to those skilled in the art without departing from the spirit and scope of the appended claims.

For example, the tissue storage lumen may be proximally peeled apart to access tissue samples and/or be transparent to allow visual inspection.

What is claimed:

1. A biopsy device, comprising:
   a probe cannula defining an internal passage;
   a proximal portion attached to the probe cannula positionable to insert the probe cannula into tissue;
   a cutter reciprocally received by the probe cannula to sever a tissue sample received in the probe cannula;
   a sample storage lumen communicating with the probe cannula, wherein the sample storage lumen has a sidewall;
   a proximal vacuum lumen communicating with the sample storage lumen via a longitudinal series of vacuum holes with the sample storage lumen;
   a vacuum tape positioned to selectively obstruct a distal portion of the longitudinal series of vacuum holes, wherein the vacuum tape extends longitudinally along the sidewall of the sample storage lumen;
   an indexing mechanism operatively configured to distally reposition longitudinal position of the vacuum tape relative to the sample storage lumen to open a proximal subset of the distal portion of longitudinal series of vacuum holes as a further proximal subset is blocked by previously collected stored tissue samples, wherein the indexing mechanism further comprises a tape wheel rotatably attached to the biopsy device, wherein the tape wheel winds the vacuum tape;
   a motor assembly operatively configured to translate the cutter to sever the tissue sample in the probe cannula; and
   a pneumatic switching assembly operatively configured to move the severed tissue sample from the probe cannula into the sample storage lumen.

2. The biopsy device of claim 1, wherein the indexing mechanism is coupled for longitudinal translating motion with the cutter and further comprises a gear mechanism operatively configured to convert the longitudinal translating motion into an intermittent rotation in one direction of the tape wheel.

3. The biopsy device of claim 1, wherein the sample storage lumen comprises a tube assembly detachable from the indexing mechanism.

4. The biopsy device of claim 1, wherein the probe cannula comprises a cylindrical probe tube having a side aperture sized to admit prolapsed tissue, the cutter comprising a cutter tube axially offset within the probe tube to closely reciprocate past the side aperture, the pneumatic switching assembly communicating a pneumatic pressure differential between a distal end of the cutter tube and the sample storage lumen that is in pneumatic communication with a proximal end of the cutter tube.

5. The biopsy device of claim 1, wherein the probe cannula comprises a cutter lumen having a side aperture, the cutter comprising a cutter tube sized to reciprocate within the cutter lumen, further comprising a lateral lumen distally communicating with the side aperture and defining an internal passage, the pneumatic switching assembly communicating a pneumatic pressure differential between distal end of the cutter tube and the proximal vacuum lumen.

6. The biopsy device of claim 1, further comprising a first motor driven carriage that translates the cutter and the indexing mechanism.

7. The biopsy device of claim 6, further comprising a second motor driven carriage that changes a pneumatic state of the pneumatic switching assembly.

8. The biopsy device of claim 1, further comprising a translation shaft rotated by the motor, and first and second motor driven carriages received on the translation shaft.

9. The biopsy device of claim 1, further comprising a frame assembly attached to the probe cannula and longitudinally movable within a cover of the biopsy device, the motor assembly further operably configured to impart a longitudinal reciprocating motion to the frame assembly during tissue penetration.

* * * * *